(12) United States Patent
Wenger et al.

(10) Patent No.: US 8,219,200 B2
(45) Date of Patent: Jul. 10, 2012

(54) MEDICAL DEVICE PACKAGING SYSTEM

(75) Inventors: William K. Wenger, St. Paul, MN (US);
Paul G. Krause, Shoreview, MN (US);
William J. Plombon, Forest Lake, MN (US); Steven N. Lu, Downingtown, PA (US); Sean B. McAdams, Minneapolis, MN (US); Brian B. Lee, Golden Valley, MN (US); Lee Stylos, Stillwater, MN (US); Judy B. Salzer, Coon Rapids, MN (US); G. Jordan Montgomery, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 245 days.

(21) Appl. No.: 12/825,798

(22) Filed: Jun. 29, 2010

(65) Prior Publication Data

US 2011/0004265 A1    Jan. 6, 2011

Related U.S. Application Data

(62) Division of application No. 11/290,775, filed on Nov. 30, 2005, now abandoned.

(51) Int. Cl.
*A61N 1/375* (2006.01)
(52) U.S. Cl. ........................................ 607/36
(58) Field of Classification Search ............... 607/36
See application file for complete search history.

(56) References Cited

U.S. PATENT DOCUMENTS

| | | | |
|---|---|---|---|
| 4,423,732 A * | 1/1984 | Tarjan et al. | 607/27 |
| 4,522,209 A * | 6/1985 | Patrick et al. | 607/57 |
| 4,545,381 A * | 10/1985 | Bournay et al. | 607/10 |
| 4,605,007 A * | 8/1986 | Heraly | 607/27 |
| 4,705,042 A * | 11/1987 | Giurtino | 607/27 |
| 5,197,468 A * | 3/1993 | Proctor et al. | 607/9 |
| 5,411,539 A * | 5/1995 | Neisz | 607/36 |
| 5,617,853 A * | 4/1997 | Morgan | 600/386 |
| 5,662,696 A * | 9/1997 | Kroll et al. | 607/116 |
| 5,987,352 A | 11/1999 | Klein et al. | |
| 6,250,309 B1 | 6/2001 | Krichen et al. | |
| 6,292,697 B1 * | 9/2001 | Roberts | 607/27 |
| 6,408,855 B1 * | 6/2002 | Berrang et al. | 128/898 |
| 6,482,154 B1 | 11/2002 | Haubrich et al. | |
| 6,622,045 B2 | 9/2003 | Snell et al. | |
| 7,194,309 B2 * | 3/2007 | Ostroff et al. | 607/36 |
| 7,996,072 B2 * | 8/2011 | Haefner | 600/512 |
| 2002/0193844 A1 * | 12/2002 | Michelson et al. | 607/48 |
| 2004/0225329 A1 | 11/2004 | Wagner et al. | |
| 2007/0119741 A1 * | 5/2007 | Wenger et al. | 206/438 |

FOREIGN PATENT DOCUMENTS

WO        WO 01-60453        8/2001

OTHER PUBLICATIONS

International Search Report, PCT/US2006/060640, May 14, 2007, 7 pages.

* cited by examiner

*Primary Examiner* — Carl H Layno
*Assistant Examiner* — Jeremiah Kimball
(74) *Attorney, Agent, or Firm* — Reed A. Duthler; Stephen W. Bauer; Evans M. Mburu

(57) ABSTRACT

A system, comprising a sterilizable package; an implantable medical device placed inside the sterilizable package; and an electrical interface electrically coupled to the implantable medical device and extending from inside the sterilizable package to outside the sterilizable package. In various embodiments, the interface may include package contacts electrically coupled to electrode terminals on the implantable medical device, patient terminals and conductors extending between the package contacts and the patient terminals.

16 Claims, 18 Drawing Sheets

MEDICAL DEVICE PACKAGING SYSTEM

RELATED APPLICATION

This application is a divisional of U.S. patent application Ser. No. 11/290,775, filed Nov. 30, 2005 entitled "MEDICAL DEVICE PACKAGING SYSTEM", herein incorporated by reference in its entirety.

TECHNICAL FIELD

The invention relates generally to implantable medical devices, and, in particular, to configurations of implantable medical device packaging systems.

BACKGROUND

Implantable medical devices (IMDs) such as cardiac pacemakers, implantable cardiovertor defibrillators (ICDs), implantable loop recorders (ILRs), implantable drug pumps, neurostimulators, etc. are generally provided by manufactures in a sterilized package. The package commonly includes an external carton or container for holding a sterilized inner tray or pouch containing the IMD. The IMD is sterilized within the inner tray or pouch using appropriate sterilization methods such as steam, gas or ultrasonic sterilization. The inner tray or pouch is generally provided with a peelable or tearable seal that can be opened to drop the sterile IMD contained therein into a sterile field without compromising the sterility of the IMD or the sterile field. For example, an IMD packaging tray having an open top may be sealed closed with a paper lid that is peeled back at the time of an implant procedure to allow the IMD to be dropped out of the tray into the sterile field.

Some packaging systems may include within the external carton or container an outer tray or pouch for carrying the sterilized inner tray or pouch. The inner tray or pouch and device contained therein may be sterilized within the outer tray or pouch. The outer tray or pouch may then be peeled open to drop the inner tray or pouch into the sterile field at the time of implant. An implanting physician or assistant may then open the inner tray or pouch within the sterile field.

Pre-implant testing, electrophysiological mapping, or system testing is commonly performed at the beginning of an implantation procedure to ensure that a patient meets implantation criteria and/or to determine an optimal implant location for the IMD and/or associated electrodes. Such testing may be performed using the IMD since using the IMD itself would generally provide the most reliable test results. However, during pre-implant testing, considerable care must be taken to ensure that the IMD and associated leads remain sterile for implantation. Once the IMD is removed from the sterile packaging, the IMD cannot be re-shelved should the patient not meet implantation criteria. As such, external equipment is often substituted for making physiological measurements or performing electrophysiological mapping. Use of external equipment for performing testing or mapping includes certain limitations, however, since the electronics of the external equipment will generally be different than the electronics of the IMD. Signals measured by external equipment may not be the same as signals measured at the same location by the IMD. Even minor signal differences can limit the usefulness or reliability of such measurements for the purposes of pre-implant tests.

Since IMDs tend to be costly devices, it is undesirable to open the IMD sterile packaging prior to knowing with reasonable certainty that the IMD is appropriate for the patient and that an acceptable implantation site for the device and/or leads can be identified. Furthermore, external equipment needed for performing pre-implant testing may not be readily available and requires extra space within the operating theater, which is often already crowded with equipment and personnel. Often a programmer that supports surface ECG recording in addition to receiving telemetry signals from the IMD is needed to perform pre-implant testing. Such full-function programmers can be bulky and costly to provide to all clinical centers.

DETAILED DESCRIPTION

In the following description, references are made to illustrative embodiments for carrying out the invention. It is understood that other embodiments may be utilized without departing from the scope of the invention. For the purposes of illustration, various embodiments of the invention are described herein in the context of IMDs used to monitor cardiac function. Such IMDs may or may not include cardiac stimulation therapy delivery capabilities. Such devices include, for example, cardiac pacemakers, which may be used for delivering a wide variety of cardiac stimulation therapies including, for example, bradycardia pacing, cardiac resynchronization therapy, extra systolic stimulation, and anti-tachycardia pacing. Such devices further include cardiovertor/defibrillators, implantable ECG recorders, and implantable hemodynamic monitors.

The scope of the invention is not limited, however, to devices configured to monitor cardiac signals. Aspects of the invention may be implemented in any IMD system in which electrical connection to the IMD electronics, prior to removing the IMD from sterilized packaging, is desired. Access to the IMD electronics may be desired for demonstration purposes, for verifying device functionality, or for performing pre-implant testing. Among the other types of IMDs in which aspects of the invention may be implemented are implantable drug pumps and neurostimulators, which are used for stimulating any portion of the central or peripheral nervous system. For example, neurostimulators may be used for controlling pain, reducing tremor, restoring muscle function, controlling incontinence, treating sleep apnea, treating digestive disorders or for vagal nerve stimulation for controlling cardiac function.

Figure 1:
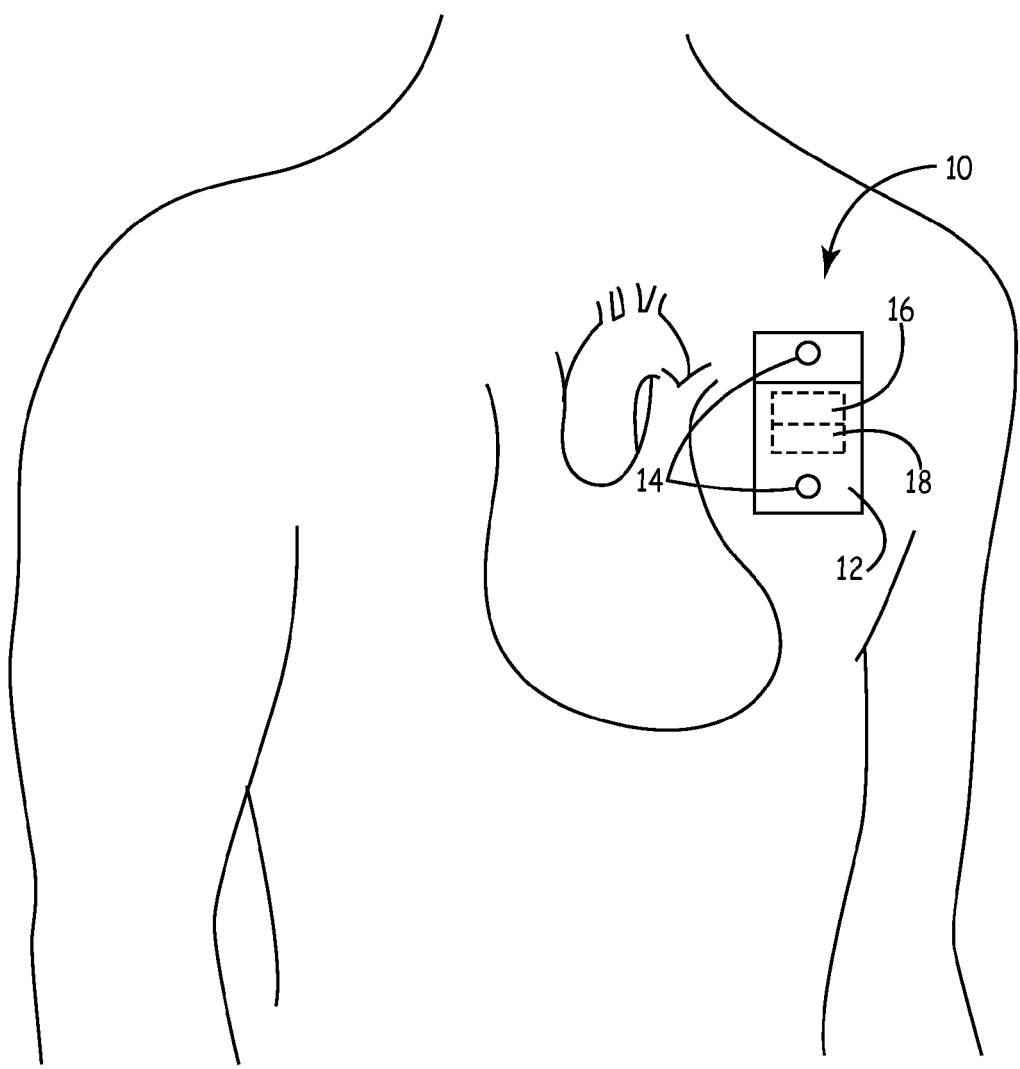
FIG. 1 is an illustration of one type of IMD in which an embodiment of the invention may be implemented.

FIG. 1 is an illustration of one type of IMD in which an embodiment of the invention may be implemented. IMD 10 is shown as an implantable ECG recorder, also referred to as an implantable loop recorder (ILR). IMD 10 is provided with a housing 12 for enclosing an electronics module 16 which controls device function and associated memory 18 for storing ECG data. IMD 10 includes two or more electrodes 14 incorporated on IMD housing 12 which function as subcutaneous ECG electrodes for the recordation of ECG signals by IMD 10. Electrodes 14 are coupled to the internal electronics module 16 such that ECG signals may be sensed by electrodes 14 and stored in memory 18, typically in a continuously looping manner. Examples of implantable cardiac monitoring devices that may be used for recording ECG data, as well as other physiological data, are generally disclosed in U.S. Pat. No. 5,987,352 (Klein et al., Nov. 16, 1999), hereby incorporated herein by reference in its entirety.

It can be appreciated that the selection of an implant site for IMD 10 is important in ensuring that the ECG signal strength is adequate. Typically, pre-implant mapping is performed using an external ECG monitor connected to electrodes placed on the surface of the patient's skin to localize a site corresponding to the strongest ECG signal strength. Since the electrodes 14 incorporated on the IMD housing 12 are relatively small compared to typical surface ECG electrodes, neonatal or pediatric-sized surface electrodes are commonly used to mimic the size and separation of the subcutaneous electrodes 14 on IMD housing 12. However, even when the subcutaneous electrode size and spacing is closely represented by the surface electrodes used for pre-implant mapping, the electronics of the external ECG monitor may bear different mapping results than when the ECG measurements are taken directly using the IMD electronics module 16.

Figure 2:
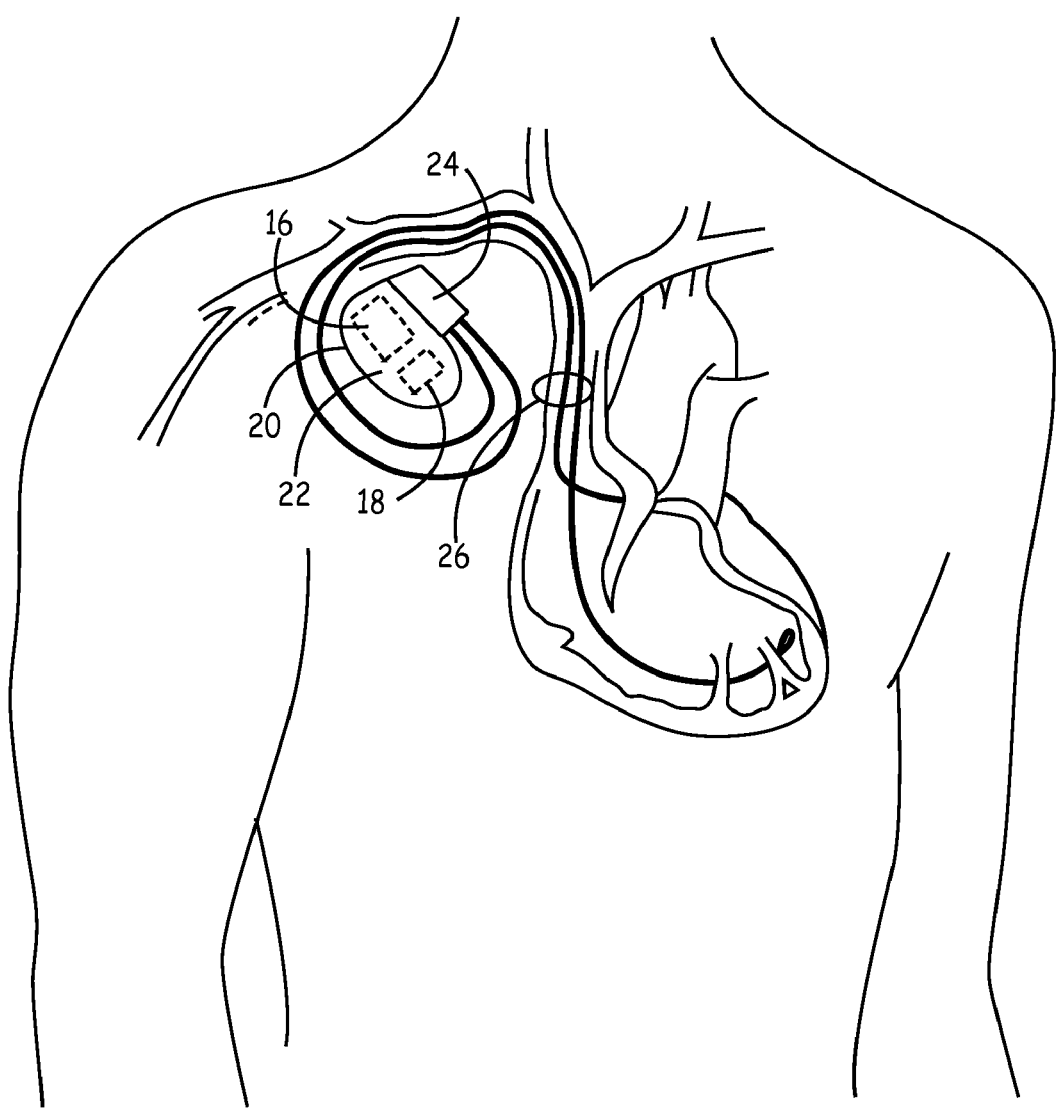
FIG. 2 is an illustration of an alternative IMD with which the invention may be practiced.

FIG. 2 is an illustration of an alternative IMD with which the invention may be practiced. IMD 20 includes a housing 22 for enclosing internal electronics 16, and a connector header 24 for receiving leads 26 disposed in operative relation to a patient's heart. Leads 26 are illustrated as transvenous leads which generally carry endocardial electrodes at or near a distal lead end. A variety of lead configurations are available for use with an IMD, which may include one or more unipolar, bipolar, or multipolar leads carrying endocardial, epicardial, subcutaneous, or other types of electrodes and/or other physiological sensors such as blood pressure sensors, pH sensors, accelerometers, etc.

Leads 26 are each provided with a proximal connector assembly having connectors corresponding to each of the electrodes/sensors carried by the individual lead. Connector header 24 includes electrical contacts which become electrically coupled to the lead connectors when the lead connector assembly is fully inserted in the connector header 24. Electrical contacts included in connector header 24 provide electrical connection between the lead connector assembly and the internal IMD electronics 16. Connection methods for connecting leads to an IMD are known in the art. An IMD may alternatively be provided with any combination of electrodes or sensors adapted for subcutaneous or non-subcutaneous implantation, either on the device housing as shown in FIG. 1 or carried by leads extending from the IMD, as generally illustrated in FIG. 2.

Figure 3:
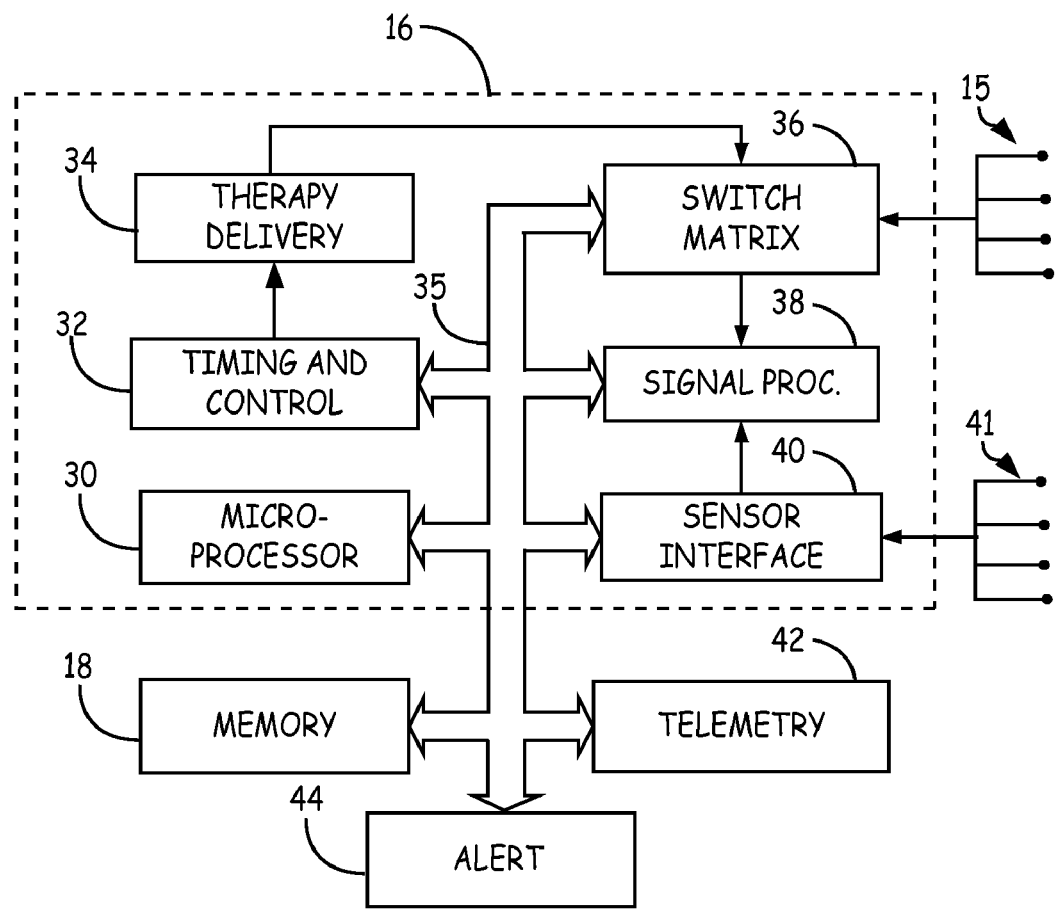
FIG. 3 is a functional block diagram representing components that may be included in an IMD electronics module along with associated memory.

FIG. 3 is a functional block diagram representing components that may be included in an IMD electronics module along with associated memory. An IMD, such as IMD 10 or IMD 20 shown in FIGS. 1 and 2 respectively, is generally provided with an electronics module 16 including timing and control circuitry 32 and an operating system that may employ microprocessor 30 or a digital state machine for timing sensing and therapy delivery functions in accordance with a programmed operating mode. Microprocessor 30 and associated memory 18 are coupled to the various components of the IMD via a data/address bus 35. If the IMD is configured to deliver a therapy, a therapy delivery unit 34 is provided which may include a pulse generator for delivering electrical stimulation or a drug reservoir and pump for delivering a drug therapy. Therapy delivery unit 34 delivers therapies as needed under the control of timing and control 32. In the case of electrical stimulation therapies, such as cardiac stimulation therapies, therapy delivery unit 34 is typically coupled to two or more electrode terminals 15, optionally via a switch matrix 36. Switch matrix 36 may be used for selecting which electrodes and corresponding polarities are used for delivering electrical stimulation pulses. The appropriate number of electrode terminals 15 is electrically coupled to electronics module 16 via feedthrough according to methods known in the art. Electrode terminals 15 may be embodied as electrodes 14 incorporated in the housing of the IMD, as shown in FIG. 1, or contacts which become electrically coupled to lead connectors as described in conjunction with FIG. 2.

Terminals 15 may also be used for coupling electrodes used for sensing electrical signals within the body to the electronics module 16. With regard to the cardiac monitoring IMD 10 shown in FIG. 1, electrode terminals 15 are embodied as subcutaneous electrodes 14 to deliver ECG signals to signal processor 38. In other embodiments, combinations of multiple subcutaneous and/or cardiac electrodes may be used for acquiring multiple ECG vectors using electrode terminals 15. Such signals may be stored in memory 18 on a continuous, periodic or triggered basis for use in diagnosing or monitoring a disease state. For example, in an ILR, heart rate and/or arrhythmia information may be determined from stored ECG signals. In devices that include therapy delivery capabilities, such as IMD 20 of FIG. 2, sensed cardiac electrical signals are also used for determining when an electrical stimulation therapy is needed and in controlling the timing of stimulation pulses.

Electrodes used for sensing and electrodes used for stimulation may be selected via switch matrix 36. When used for sensing, electrode terminals 15 are coupled to signal processing circuitry 38 via switch matrix 36. Signal processor 38 includes sense amplifiers and may include other signal conditioning circuitry and an analog to digital converter. Electrical signals may then be used by microprocessor 30 for detecting physiological events, such as detecting and discriminating cardiac arrhythmias. In other embodiments, electrical signals sensed at electrode terminals 15 may be used for measuring impedance signals for monitoring edema, respiration or heart chamber volume.

One or more physiological sensors 41 may optionally be included. Such sensors may include pressure sensors, accelerometers, impedance sensors, flow sensors, blood chemistry sensors, activity sensors or other physiological sensors known for use with IMDs. Sensors 41 are coupled to electronics module 16 via a sensor interface 40 which provides sensor signals to signal processing circuitry 38. Sensor signals are used by microprocessor 30 for detecting physiological events or conditions. For example, an IMD may monitor heart wall motion, blood pressure, blood chemistry, respiration, or patient activity. Monitored signals may be used for sensing the need for delivering a therapy under control of the operating system.

The operating system includes associated memory 18 for storing a variety of programmed-in operating mode and parameter values that are used by microprocessor 30. The memory 18 may also be used for storing data compiled from sensed physiological signals and/or relating to device operating history for telemetry transmission upon receipt of a retrieval or interrogation instruction. These functions and operations are known in the art, and are generally employed to store operating commands and data for controlling device operation and for later retrieval to diagnose device function or patient condition.

Telemetry circuitry 42 is typically provided to enable bidirectional communication between the IMD and an external programmer, home monitor, patient activator, or other external device, according to methods and apparatus known in the art. Programming commands or data are transmitted during uplink or downlink telemetry between IMD telemetry circuitry 42 and external telemetry circuitry included in a programmer or monitoring unit. According to one embodiment of the invention, pre-implant test data is obtained using a packaging system that enables connection to electronics module 16 through a sterile IMD package. Pre-implant test data so obtained can be transmitted in real time, or at a delayed time, to an external monitor/programmer using telemetry circuitry 42. Telemetry circuitry 42 may correspond to telemetry systems known in the art, and may be configured for long-range telemetry communication with a monitor/programmer. Long-range telemetry systems are generally disclosed in U.S. Pat. No. 6,482,154 issued to Haubrich et al., incorporated herein by reference in its entirety.

In some embodiments, an alert unit 44 is provided for generating an audible tone or sound. As will be described in greater detail below, electronics module 16 may be used to perform pre-implant testing using a flexible circuit or other coupling appliance for connecting external electrodes to terminals 15 without compromising the sterility of IMD within a sterile package. Microprocessor 30 may process signals received at terminals 15 for determining if implantation criteria are met or for identifying an optimal implantation location or orientation. Alert unit 44 may be used to generate an audible tone or sound to indicate to a clinician that a particular test location or orientation meets or does not meet implant criteria or acceptable signal quality.

It is recognized that the overall complexity of electronics module 16 and other IMD components may vary depending on the functionality provided by the IMD. Functional units may be added or removed from the block diagram represented in FIG. 3 according to a particular application. For example, IMD 10 shown in FIG. 1 may be used for ECG monitoring without therapy delivery capabilities in which case electronics module 16 is provided without therapy delivery unit 34. In other embodiments, a leadless IMD incorporating electrodes in the IMD housing may include pacing and/or cardioversion/defibrillation capabilities in which case therapy delivery unit 34 would include a low-voltage pulse generator and/or high-voltage capacitors with associated capacitor charging and high-voltage output circuitry as is known in the art.

Figure 4A:
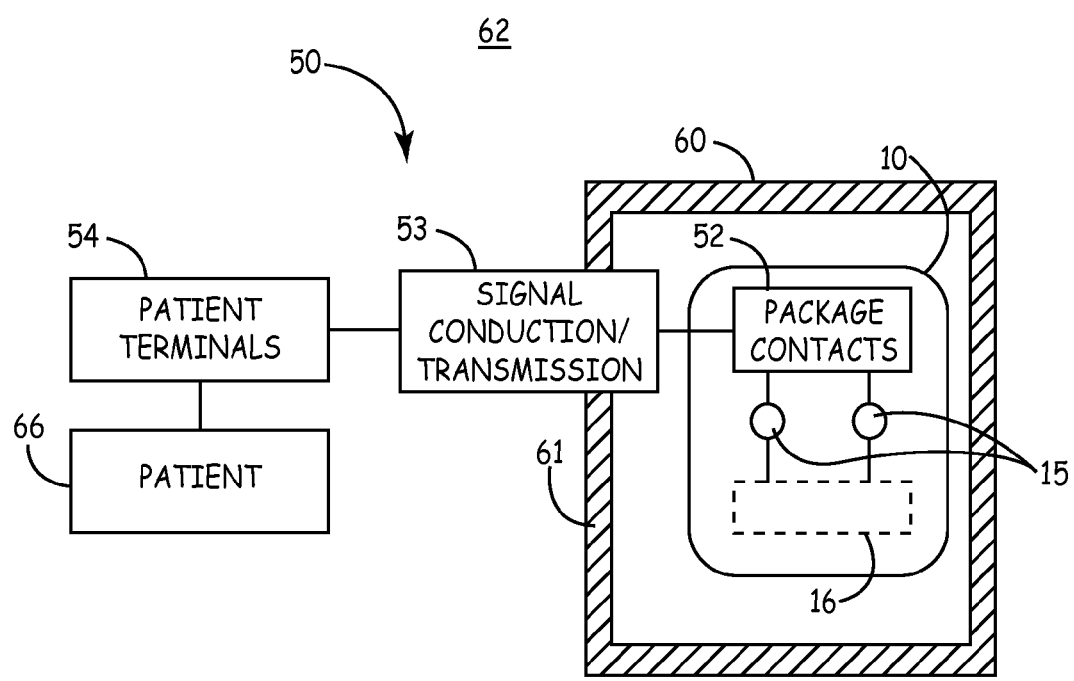
FIG. 4A is a block diagram providing an overview of an IMD packaging system including an electrical interface according to various embodiments of the invention.

FIG. 4A is a block diagram providing an overview of an IMD packaging system according to various embodiments of the invention. The packaging system 62 includes a sterilizable package 60 for containing an IMD 10. Packaging system 62 further includes an electrical interface 50 that allows electrodes or other sensors placed on or in a patient 66 to be coupled to electronics module 16 while IMD 10 remains with sterilizable package 60, without compromising the sterility of IMD 10.

Electrical interface 50 includes patient terminals 54, signal/conduction transmission 56, and package contacts 52. Patient terminals 54 may be in the form of electrodes adapted for placement directly on or in patient 66. Alternatively, patient terminals 54 may be provided as connectors, such as snaps or clips, onto which electrodes or sensors placed on or in patient 66 may be attached using a cable, extension or lead. One or more package contacts 52 are electrically coupled to IMD electrode terminals 15 (or sensor terminals 41) included in IMD 10 and thereby electrically coupled to electronics module 16. As described previously, IMD electrode terminals 15 may be embodied as electrodes formed in or on the housing of IMD 10. IMD electrode terminals 15 may alternatively be embodied as contacts used for electrically coupling lead-based electrodes and/or sensors to IMD 10. The number of package contacts and corresponding patient terminals provided will depend on the application and may correspond to the total number of electrodes and sensors used by the IMD or a subset of electrodes and sensors used by the IMD.

Electrical interface 50 includes signal conduction/transmission 56 which acts to convey signals received from the patient at patient terminals 54 to package contacts 52, across a sterile barrier 61 of package 60. Signal conduction/transmission 53, generally referred to as "conductor circuit" hereafter, may include conductors in the form of wires, foils, conductive tape, film or ink. However, it is recognized that conductor circuit 53 is not limited to include only conductive elements. In various embodiments, conductor circuit 53 may include inductive elements, capacitive elements, antennas, optical fibers, or any other elements appropriate for conducting or transmitting a physiological signal received at patient terminals 54 to package contacts 52. Alternatively, signals may be transmitted from IMD electronics module 16 to patient 66 using electrical interface 50. Depending on the type of sensors used by IMD 10, electrical excitation signals may be required and transmitted to a sensor operatively positioned in patient 66 via electrical interface 50. During some pre-implant testing, system tests or demonstration procedures, electrical pulses, for example stimulation pulses, may be transmitted from electronics module 16 to patient terminals 54.

Figure 4B:
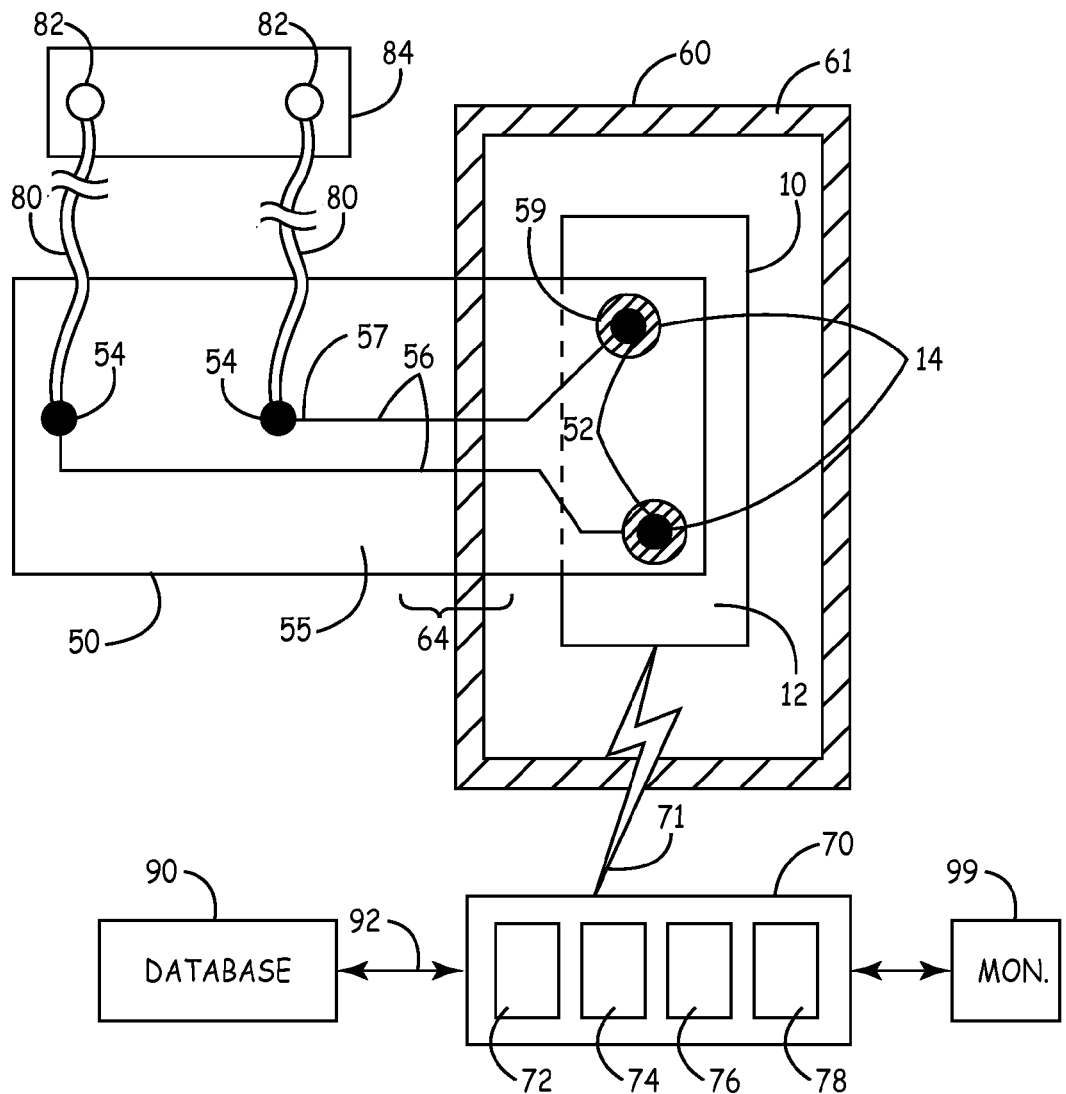
FIG. 4B is a diagram of an IMD packaging system wherein an electrical interface is provided in the form of a flexible circuit.

FIG. 4B is a diagram of an implantable medical device packaging system wherein electrical interface 50 is provided in the form of a flexible circuit that allows access to the IMD electronics module 16 while the IMD 10 is enclosed in a sterilizable package 60. The packaging system includes electrical interface 50 extending from outside sterilizable package 60 to inside sterilizable package 60. Electrical interface 50 includes one or more package contacts 52 each coupled to individual conductors 56 included in conductor circuit 53, and one or more patient terminals 54. Each of conductors 56 extend across sterile barrier 61, between an interior end 59 coupled to a package contact 52 and an exterior end 57 coupled to a patient terminal 54.

In the embodiment shown, package contact 52 is disposed over a subcutaneous electrode 14 located on IMD housing 12 while the IMD remains in package 60. Package contact 52 makes electrical connection with electrode 14 thereby allowing electrical connection to the electronics contained in IMD 10 using patient terminal 54, located outside of sterilizable package 60. In various embodiments, package contact 52 may be adapted for electrical coupling to any electrode or any electrode/sensor terminal or contact incorporated in or on IMD 10.

Sterilizable package 60 is provided as a tray, pouch or other container for enclosing and maintaining sterility of IMD 10. Sterilizable package 60 is typically sealed closed after receiving IMD 10 to form sterile barrier 61 and submitted to a sterilization method appropriate for the particular IMD contained therein, e.g., steam, gas, or ultrasonic sterilization. Electrical interface 50 conveys electrical signals received at patient terminals 54 across sterile barrier 61 without compromising the integrity of the sealed package 60 or the sterility of the IMD 10.

Electrical interface 50 may be fabricated as a flexible circuit using conductive ink (e.g., silver-silver chloride ink or a carbon-based ink) printed on a flexible, insulative substrate 55 to form conductors 56, package contacts 52 and patient contacts 54. Alternatively, any of conductors 56, package contacts 52 and patient contacts 54 may be formed by laminating or adhering electrically conductive materials in the form of wires, foils, film, or tape, onto flexible substrate 55. As will be described in greater detail below, in some embodiments flexible substrate 55 includes a portion of sterilizable package 60 wherein electrical interface 50 is formed on a surface of package 60.

Patient terminals 54 may be provided for direct placement on a patient's skin. Electrical body signals may then be provided to IMD 10 via electrical interface 50. Electrical interface 50 is provided with a "neck" 64 along which conductors 56 extend. Neck 64 may be provided with any length to facilitate unencumbered placement of patient terminals 54 on a patient. Alternatively, patient terminals 54 may be embodied as coupling terminals or contacts to which electrode cables or extensions 80 may be attached to thereby allow greater maneuverability and flexibility during pre-implant testing, without patient-to-IMD distance limitations. Electrode extensions 80 may be standard surface electrode cables carrying surface electrodes 82, which may be standard "off-the shelf" electrodes, adapted for placement on a patient's skin.

Patient terminals 54 may alternatively be adapted for electrical coupling to patient leads or lead extensions. For example, extensions 80 may be provided with snaps, alligator clips, manufacturer-provided connectors, or other electrical connectors for facilitating electrical connection to patient terminals 54 at one end of an extension 80 and to a connector assembly of an implanted lead at the other end of an extension 80. Extensions 80 may be provided in a sterile condition to allow connection to implanted sterile leads. It is recognized that numerous configurations may be used for connecting patient terminals 54 to a patient, either directly or indirectly using extensions and/or leads, and such embodiments may include any number of electrodes and/or sensors positioned on or in the patient.

A template 84 may be provided for guiding placement of surface electrodes 82 to correspond to the separation distance of IMD electrodes 14. Alternatively, electrode extensions 80 and surface electrodes 82 may be custom components, provided with template 84 for mimicking the size and separation of IMD electrodes 14. Patient terminals 54 may be provided as snaps, clips, or any other mechanism for mechanically and electrically coupling electrode extensions 80. Template 84 may include labeling to indicate which patient terminals 54 correspond to which IMD electrode terminals 15 and/or sensor terminals 41.

During pre-implant testing, signals obtained during placement of patient terminals 54 at different body locations and orientations may be stored and analyzed by IMD 10 for determining an optimal implant location. Alternatively or additionally, IMD 10 may transmit signals received using electrical interface 50 to an external programmer/monitor 70 via a telemetry connection 71.

External programmer/monitor 70 may correspond generally to programmer/monitors known in the art and typically includes telemetry circuitry 72, a microprocessor-based control system 74, a display 76, and a user-interface 78, which may be embodied as a graphical user interface. Display 76 may be in the form of an LCD screen or other graphical or video display that allows a clinician to observe displayed signal data, for example ECG signals, while patient terminals 54 are positioned at different body locations or orientations. The clinician may manually select an optimal implant location based on observed data.

Alternatively, external programmer/monitor 70 or IMD 10 may analyze received signals using a programmed signal evaluation routine and automatically recommend an implant site or at least indicate when a location or orientation meets signal quality or other implant criteria. Such information can be displayed graphically or using text messages on display 76. Alternatively, display 76 may be embodied as an LED display which indicates through color or number of LEDs illuminated acceptable on unacceptable signal quality. In yet another embodiment, display 76 may include a speaker for broadcasting sound messages indicating acceptable or unacceptable signal quality. As described previously, alert circuitry 44 may generate a signal indicating acceptable or unacceptable signal quality. A signal evaluation routine may determine signal features, signal-to-noise ratio, or other signal characteristics for determining if the signal quality meets predefined acceptance criteria.

Display 76 may further be used to prompt a clinician or other user to move patient terminals 54 to a number of body locations or orientations while IMD 10 and/or external monitor/programmer 70 collects signal data corresponding to each location. The clinician or other user may use user interface 78 to indicate to IMD 10 or external monitor/programmer 70 when patient terminals 54 are being moved to a new location and thereby indicate when IMD 10 or external monitor/programmer 70 should begin a new signal evaluation routine. When multiple electrodes or sensors are available and coupled simultaneously to IMD 10 using patient terminals 54, the IMD 10 may select different sensing vectors using switching circuitry 36 (shown in FIG. 3), either automatically or in response to programmed-in commands.

External programmer/monitor 70 may vary in functionality and complexity in different embodiments. For example, in some embodiments, external programmer/monitor 70 may receive signal data using telemetry circuit 72, process signal data using microprocessor 74, and display pre-implant test results on display 76. External programmer/monitor 70 may include a data storage module for printing or storing received data and/or test results electronically. In other embodiments, external programmer/monitor 70 may be interfaced with a monitoring device 94 used for displaying and/or storing signal data obtained using electrical interface 50.

In still other embodiments, external programmer/monitor 70 may serve as a communication conduit between IMD 10 and a computerized database 90. Database 90 may be a web-based patient management system or implemented on a personal computer. Database 90 is coupled to a communication network 92, which may be a wireless network, enabling communication between database 90 and external programmer/monitor 70. Signal data received by external programmer/monitor 70 is transmitted to database 90 via communication network 92. As such, signals obtained using electrical interface 50, or test results based on such signals, may be transmitted directly to database 90 for further analysis and/or viewing by a user. Database 90 may be accessible on a local or remote computer, allowing pre-implant testing to be performed in a time and place independent manner. Database 90 and external programmer/monitor 70 may be provided according to known patient management systems, such as those generally disclosed in U.S. Pat. No. 6,250,309 (Krichen, et al.) and U.S. Pat. No. 6,622,045 (Snell et al.), both of which patents are incorporated herein by reference in their entirety.

Figure 5:
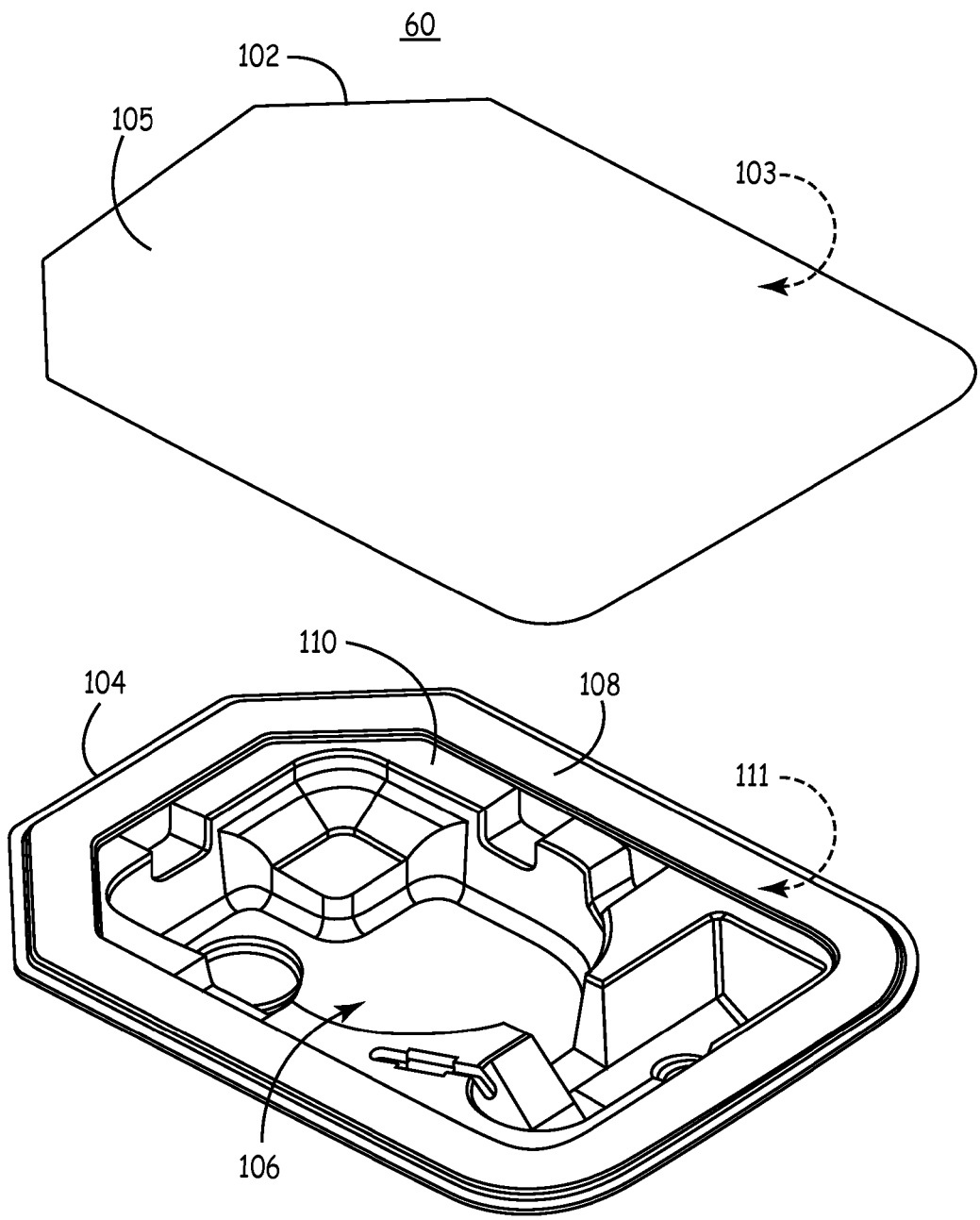
FIG. 5 is a perspective view of one type of sterilizable package that may be used in various embodiments of the invention.

FIG. 5 is a perspective view of one type of sterilizable package that may be used in various embodiments of the invention. Package 60 includes a tray 104, typically provided with a cavity 106 formed to match the contours of an IMD to be placed therein. Package tray 104 has an inner surface 110 and an outer surface 111 which, in addition to cavity 106, may form other cavities or recesses for containing accessories, tools or other components packaged with the IMD for use during implantation procedures. Tray 104 is fabricated using thermoforming, injection molding or other appropriate processing of a material that withstands sterilization procedures used to sterilize the IMD contained therein and acts as a sterile barrier there after. Packaging tray 104 is commonly fabricated from high-density polyethylene.

Tray 104 includes a seal area 108 along inner surface 110 onto which a tray lid 102 is sealed after the IMD and any other package contents are placed in tray 104. Tray lid 102 includes an outer surface 105 and an inner surface 103 and is commonly fabricated from coated paper or a high-density woven or non-woven polymer material. Tray lid 102 and tray 104 are typically sealed together along seal area 108 using an appropriate adhesive for forming a reliable sterile barrier. After undergoing sterilization, package 60 is placed in any desired outer packaging, which is typically a box or carton provided with appropriate labeling. In some embodiments, the packaging system may include an outer tray and outer tray lid for containing inner tray 104 sealed with inner tray lid 102. Inner tray 104 may be sterilized within the outer tray, and the outer tray is placed in the desired outer packaging.

Figure 6A:
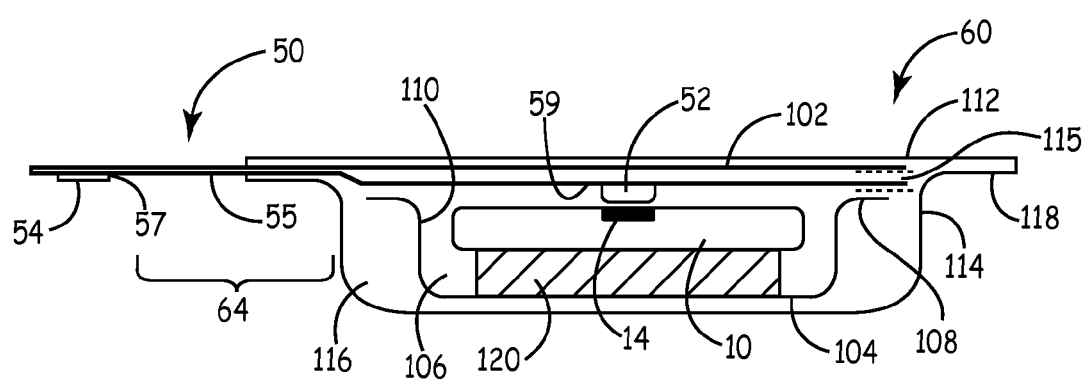
FIG. 6A is a side cut-away view of one embodiment of a packaging system including an electrical interface used for accessing IMD electronics while the IMD is contained within a sterile package.

FIG. 6A is a side cut-away view of one embodiment of a packaging system including an electrical interface used for accessing IMD electronics while the IMD is contained within a sterile package 60. Sterile package 60 includes an inner tray 104 and outer tray 114. IMD 10 rests in cavity 106 of inner tray 104. An electrical interface 50 in the form of a flexible circuit 50 is placed over IMD 10 such that package contact 52 is electrically coupled to IMD electrode 14. Inner tray 104 is sealed closed with inner tray lid 102 along seal area 108. Inner tray 104 is placed within a tray cavity 116 of outer tray 114. Outer tray 114 is sealed closed with outer tray lid 112 along outer tray seal area 118. The neck 64 of electrical interface 50 is sealed between inner tray lid 102 and inner tray 104 and between outer tray lid 112 and outer tray 114 and extends outside of package 60. Patient terminals 54 are located at the exterior ends 57 of conductors 56 extending along neck 64. Patient terminals 54 are thus available outside of package 60 for use in coupling a patient to the electronics module contained within IMD 10, without compromising the sterility of IMD 10 within package 60.

The depth of IMD cavity 106 in inner tray 104 is dimensioned appropriately to cause electrode 14 to come into contact with package contact 52 when the packaging system 62 is assembled. To promote reliable coupling between package contact 52 and IMD electrode 14, the thickness 115 of substrate 55, at least in the area of package contact 52, is provided to create pressure between contact 52 and IMD electrode 14. Package contacts 52 may be formed as blisters or buttons, having a generally hemispherical shape, for example, which protrudes from flexible circuit substrate 55 to thereby promote reliable electrical contact with IMD electrodes 14.

Additionally or alternatively, a compressible element 120 may be included or incorporated in inner tray 104. Physical contact between package contact 52 and IMD electrode 14 should be adequate to create an electrical connection between contact 52 and electrode 14 without causing mechanical damage to electrode 14. As shown, compressible element 120, which may be embodied as a compressed foam member, is placed between the inner surface 110 of inner tray 104 and IMD 10. Compressible element 120 generates pressure between IMD electrode 14 and package contact 52 to promote reliable electrical contact there between. Compressible element 120 could alternatively be positioned between the inner surface 103 of inner tray lid 102 and electrical interface 50 or along the outer surface 105 of inner tray lid 102, between inner tray lid 102 and outer tray lid 112. Compressible element 120 may alternatively be enclosed in an outer carton containing package 60 and positioned to generate pressure in the area of package contact 52 and IMD electrode 14.

Figure 6B:
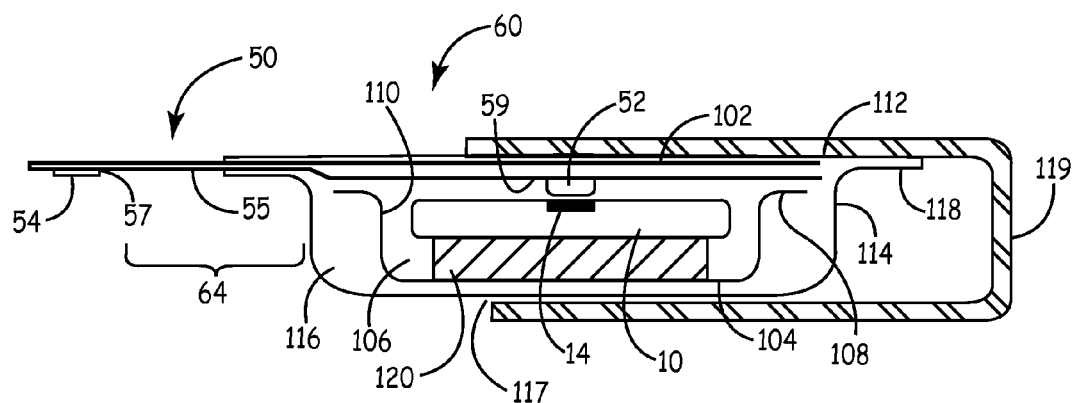
FIG. 6B is a side, sectional view of an alternative embodiment of packaging system including a pressure generating member for promoting reliable electrical contact between an electrical interface and an IMD enclosed in a sterile package.

FIG. 6B is a side, sectional view of an alternative embodiment of packaging system including a pressure generating member 121 for promoting reliable electrical contact between electrical interface 50 and IMD 10 enclosed in sterile package 60. In FIG. 6B, pressure generating member 121 is provided as a generally U-shaped clip having a closed side 119 and an open side 117. Pressure generating member 121 is adapted for positioning around the outside of outer tray 114 and outer tray lid 118 to generate positive pressure in the area of package contact 52 and IMD electrode 14 to promote good electrical contact there between.

Figure 6C:
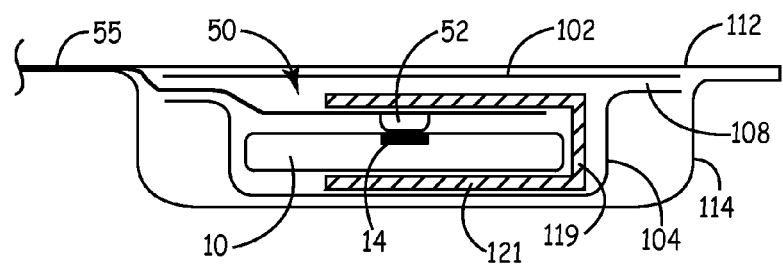
FIG. 6C shows a pressure generating member 121 packaged within an inner tray, around an IMD and electrical interface for promoting good electrical contact between the IMD and electrical interface.

Pressure generating member 121 may be packaged in an outer carton along with sterile package 60 and placed in the position shown in FIG. 6B by a user as needed at the time of testing. Alternatively, pressure generating member 121 may be packaged with sterile package 60 already positioned around sterile package 60 as shown in FIG. 6B. In other embodiments, pressure generating member 121 may be positioned within outer tray 114, around inner tray 104 and inner tray lid 102 to promote good electrical contact between package contact 52 and IMD electrode 14. Pressure generating member 121 could alternatively be packaged within inner tray 104, around IMD 10 and electrical interface 50 as shown in FIG. 6C. In this embodiment, electrical interface 50 would not be sealed along its entire periphery between inner tray lid 102 and inner tray 104 in order to allow pressure generating member 121 to be fitted over one side or end of electrical interface 50 as shown. Pressure generating member 121 may also act to stabilize the position of electrical interface 50 relative to IMD 10.

Pressure generating member 121 may be formed of a relatively rigid polymeric or metal material which may be flexible along closed side 119 to allow open side 117 to be opened wider to enable member 121 to be slid over the outside of sterile package 60 (or inner tray 104 and tray lid 102 or IMD 10 and electrical interface 50). It is recognized that pressure-generating member 121 may be provided in numerous configurations for promoting good contact between electrical interface 50 and IMD 10. For example, pressure generating member 121 may alternatively be formed having a "clamshell" shape, having a hinged or spring-loaded side or sides, or having latching mechanisms. Pressure generating member 121 may be used alone or in combination with compressible element 120. Pressure generating member 121 and/or compressible element 120 may be designed to create a predetermined, constant pressure at the contact point between IMD 10 and electrical interface 50.

Figure 7:
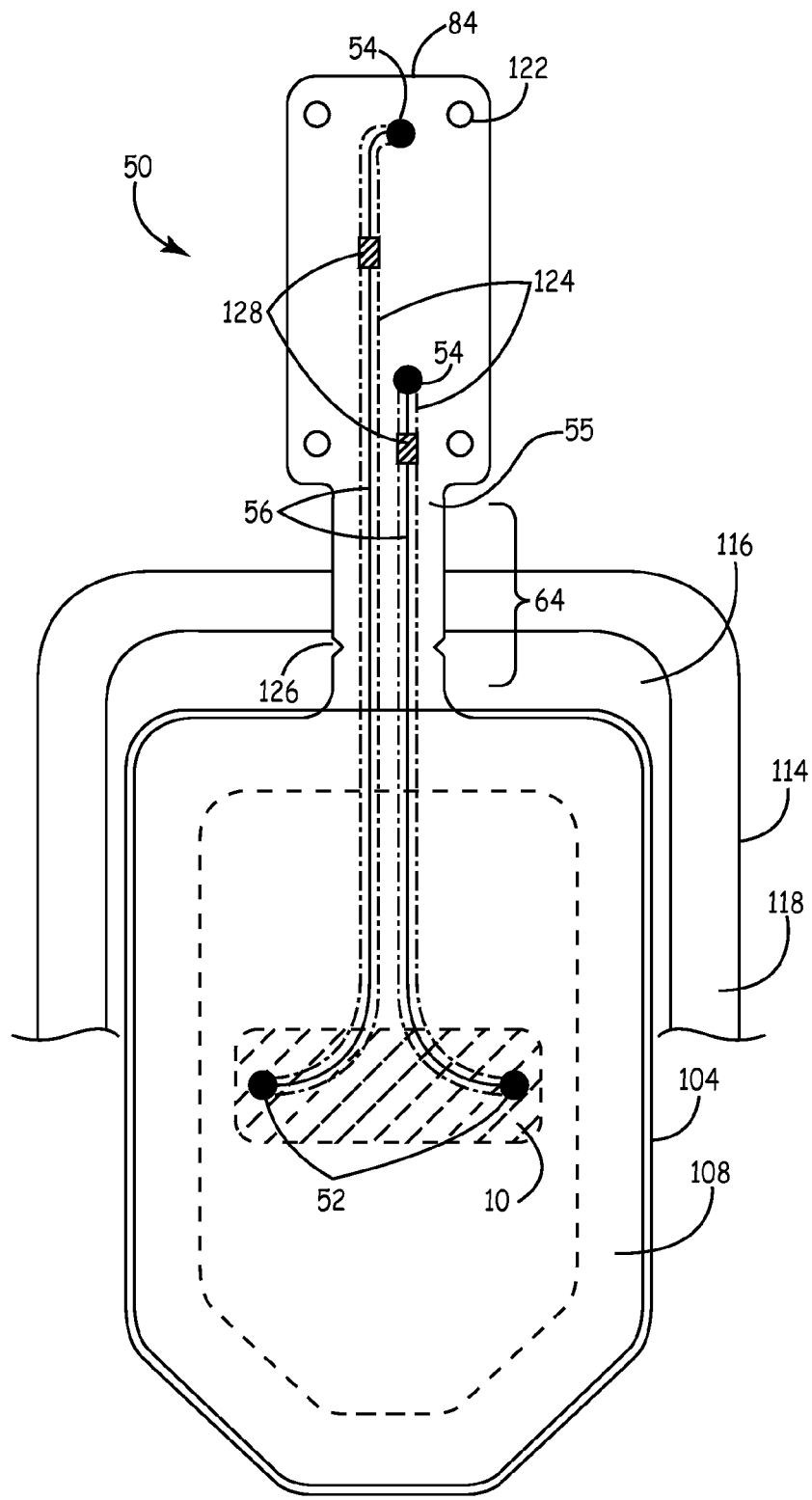
FIG. 7 is a top view of the packaging system shown in FIG. 6A.

FIG. 7 is a top view of the packaging system shown in FIG. 6A. Electrical interface 50 includes a flexible substrate 55 that may be formed to match the outer contours of the inner tray 104. Substrate 55 becomes sealed between inner tray 104 and inner tray lid 102 (shown in FIG. 6A) along the entire seal area 108. Providing substrate 55 along the entire seal area 108 may prevent thickness differentials along seal area 108 that might otherwise leave discreet openings along the seal area 108 which could lead to contamination of the inner tray contents. Alternatively substrate 55 may be formed such that substrate 55 is sealed between inner tray 104 and inner tray lid 102 along any portion of seal area 108, as long as a reliable seal is formed between tray 104 and tray lid 102 for maintaining sterility of IMD 10 and any other packaged components. Generally, substrate 55 will be sealed between tray 104 and lid 102 at least along the area where neck 64 of electrical interface 50 traverses inner seal area 108

Conductors 56 may be insulated by a dielectric layer 124 formed over conductors 56. Dielectric layer 124 may additionally extend over any portion or all of substrate 55, while leaving package contacts 52 and patient contacts 54 exposed. Dielectric layer 124 may extend over the entire inner tray seal area 108 to promote a uniform, reliable seal. Dielectric layer 124 may be formed from any dielectric polymeric material including polyesters, ethylene-vinyl acetate copolymers, terpolymers such as acrylonitrile-butadiene styrene, or polyvinyl chloride and its copolymers. Alternatively, conductor circuit 53 may include shielded conductors and contacts to protect the IMD and/or patient from electrical noise.

The exterior end of substrate 55 may be formed into a template 84 upon which patient contacts 54 are mounted. Template 84 corresponds to the size and shape of IMD 10 with patient contacts 54 sized and spaced relative to one another to mimic the size and spacing of IMD electrodes 14.

Once an optimal implant site is identified through pre-implant testing, the site may be marked or traced using template 84. Template 84 may be provided having stencil openings 122 to facilitate marking a selected implant site on a patient.

In FIG. 7, conductor circuit 53 is shown to include LEDs 128 along each conductor 56. LEDs 128 may be used to indicate that an electrical circuit has been completed and signals received at patient terminals 54 are being conducted to IMD 10. In some embodiments, the IMD 10 may transmit signals to patient terminals 54, such as sensor excitation signals or electrical stimulation pulses. As such, LEDs 128 may be used to indicate that electrical signals from IMD 10 are being conducted to patient terminals 54.

After completing pre-implant testing, the outer tray lid may be removed from outer tray 114. Neck 64 of electrical interface 50 may be provided with notches or perforations 126 to facilitate tearing of the electrical interface 50 just outside of inner tray 104. Tearing of electrical interface 50 allows inner tray 104 to be removed from outer tray 114 without hindrance due to attachment of electrical interface 50 to outer tray 114 along outer tray seal area 118.

Figure 8:
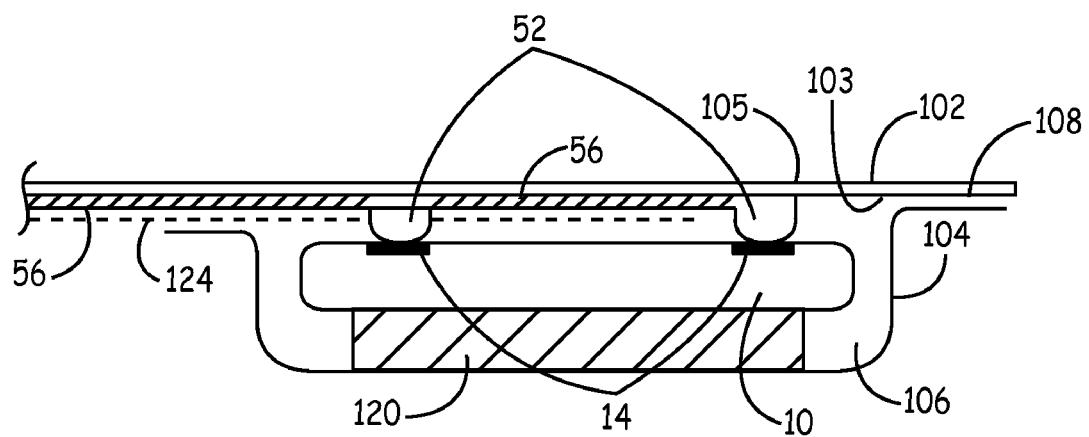
FIG. 8 is a partial, side, cut-away view of an IMD packaging system according to an alternative embodiment of the invention wherein an electrical interface is formed on a substrate that includes a surface of the sterilizable package.

FIG. 8 is a partial, side, cut-away view of an IMD packaging system according to an alternative embodiment of the invention wherein an electrical interface is formed on a substrate that includes a surface of the sterilizable package. In this example, inner surface 103 of inner tray lid 102 serves as a substrate for electrical interface 50. In this embodiment, conductors 56 and package contacts 52 are shown printed or laminated to inner surface 103 of inner tray lid 102. Conductors 56 may be insulated by a dielectric layer 124.

Figure 9:
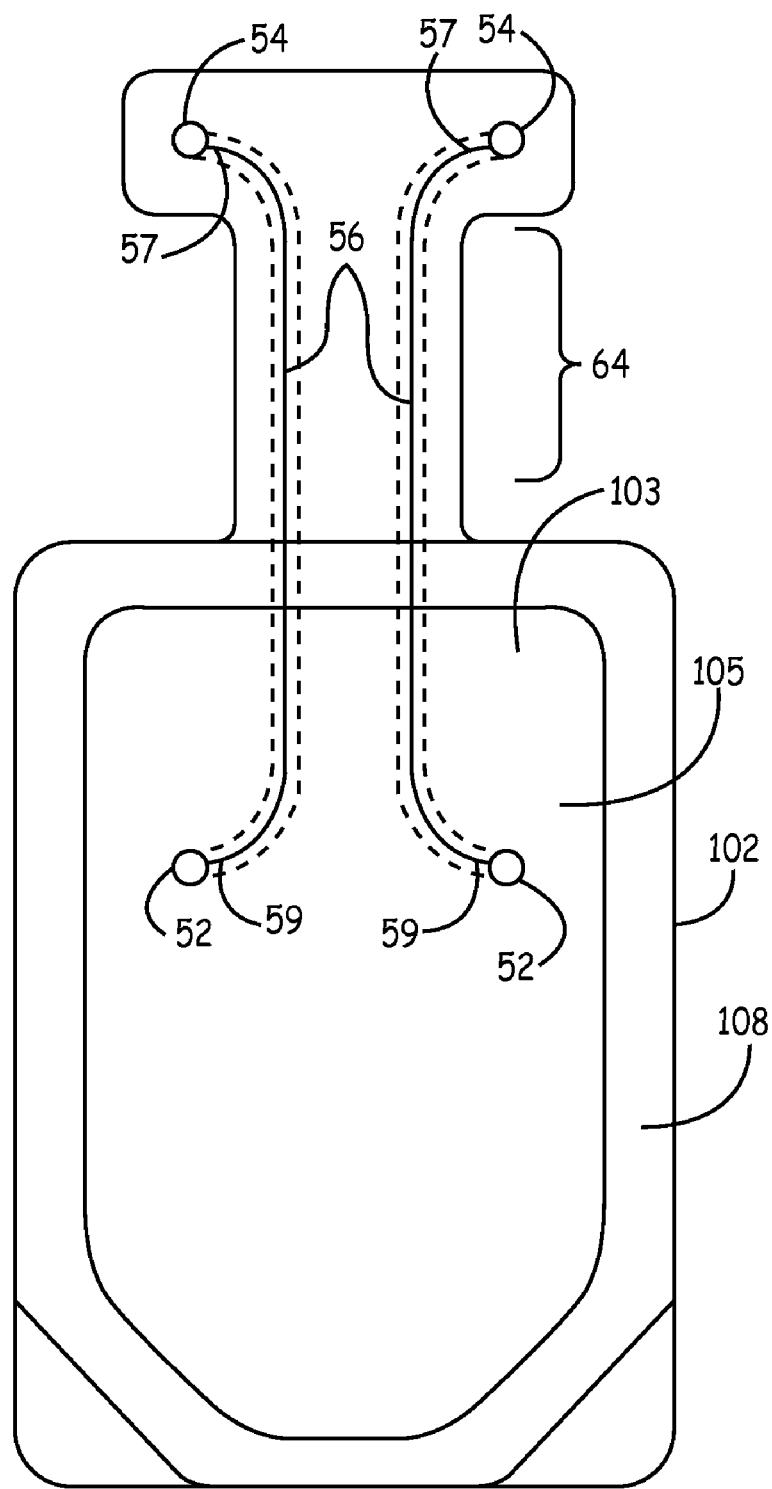
FIG. 9 is a bottom view of the inner tray lid shown in FIG. 8.

FIG. 9 is a bottom view of the inner tray lid shown in FIG. 8. Tray lid 102 is provided with a shape that mates with the seal area 108 of inner tray 104 (shown in FIG. 5) and serves as a substrate for electrical interface 50. Inner tray lid 102 is formed with neck 64 extending there from with patient terminals 54 coupled to the exterior ends 57 of conductors 56. Inner tray lid 102 may be fabricated from paper or a high-density, woven or non-woven polymer, such as a high-density polyethylene. Conductors 56, patient terminals 54 and package contacts 52 may be printed on inner tray lid 102 using a conductive ink or may be provided as foil, tape, film conductive material laminated to tray lid 102. In some embodiments, the inner surface 103 of inner tray lid 102, or any other substrate onto which electrical interface 50 is formed, may be bonded or treated with a coating to promote good adhesion of the conductive material on the substrate. The tray lid 102 is coated with an adhesive along seal area 108 for sealing lid 102 to inner tray 104.

Figure 10A:
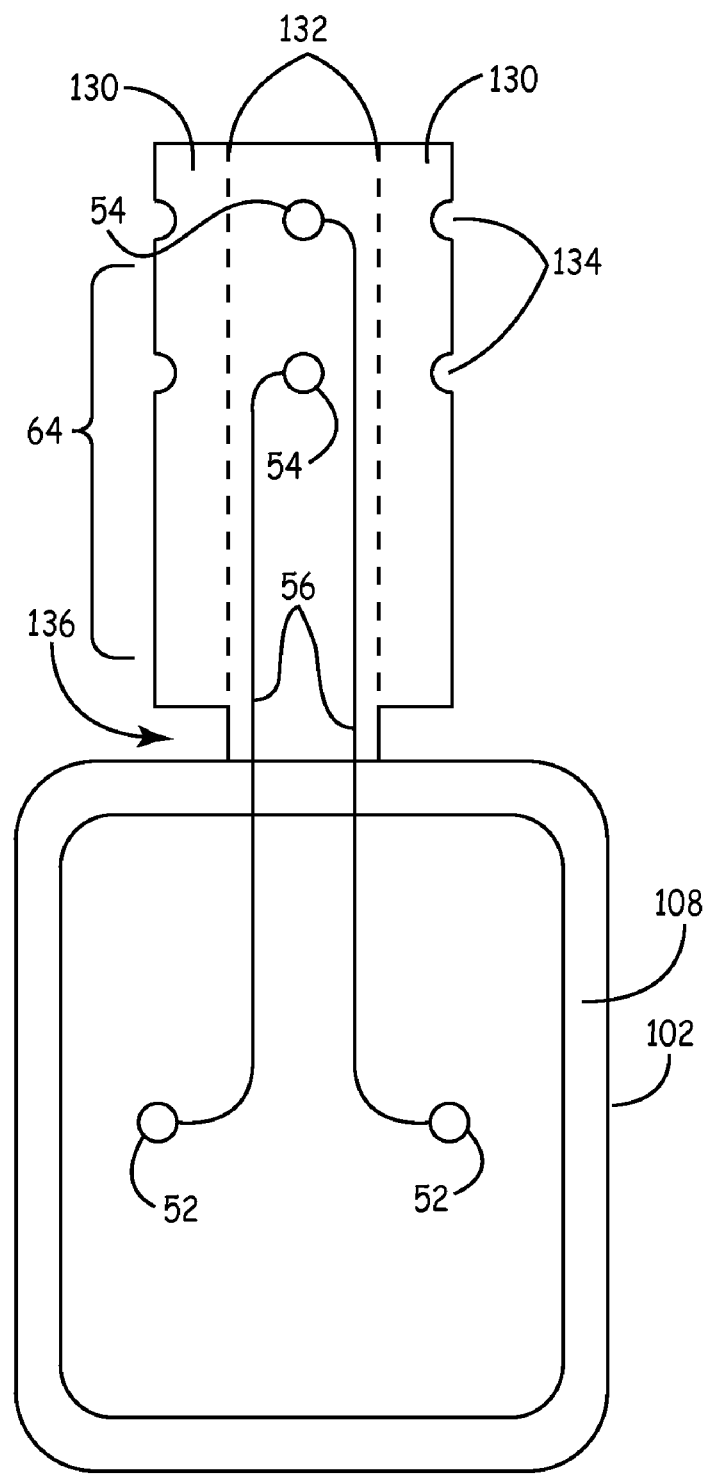
FIG. 10A is a top view of an alternative embodiment of a flexible circuit electrical interface formed on the inner surface of an inner tray lid.
Figure 10B:
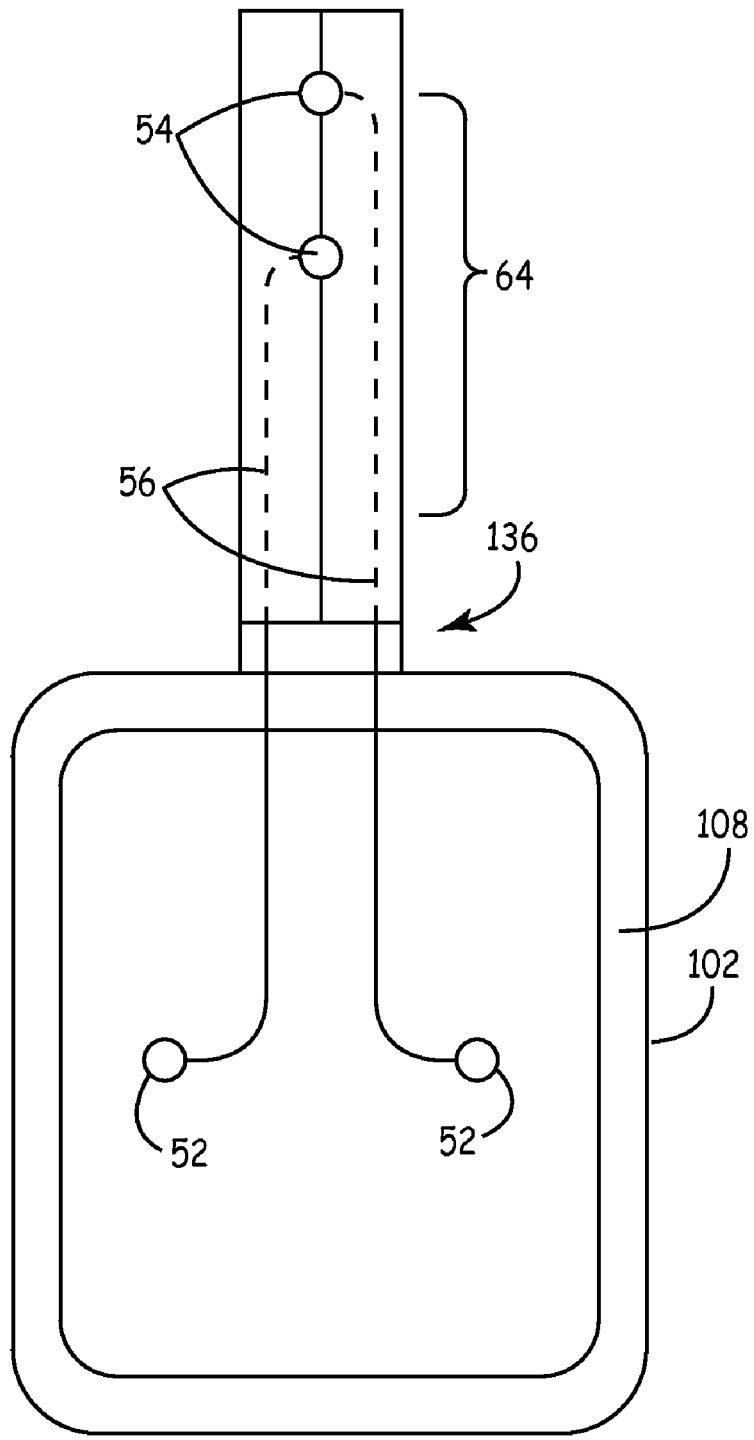
FIG. 10B is a top view of the flexible circuit shown in FIG. 10A after folding the flexible substrate along fold lines to provide insulation to the exterior portions of conductors.

FIG. 10A is a top view of an alternative embodiment of an electrical interface formed on the inner surface of an inner tray lid. The substrate 55 is formed with lateral flaps 130 along neck 64 which can be folded along fold lines 132 over elongated conductors 56 thereby providing insulation to conductors 56. Lateral flaps 130 are formed having patient electrode windows 134 such that when lateral flaps 130 are folded along fold lines 132, patient electrodes are exposed and not insulated by lateral flaps 130. A portion 136 of neck 64 corresponding to the seal area 108 of an outer tray, when used, is provided without lateral flaps 130. The portions of conductors 56 that become enclosed within inner tray 104, inner tray seal area 108, and outer tray seal area 118 may not need to be insulated and may remain exposed. FIG. 10B is a top view of the electrical interface shown in FIG. 10A after folding substrate 55 along fold lines 132 to provide insulation to the portions of conductors 56 which will be located outside of an outer tray.

Figure 10C:
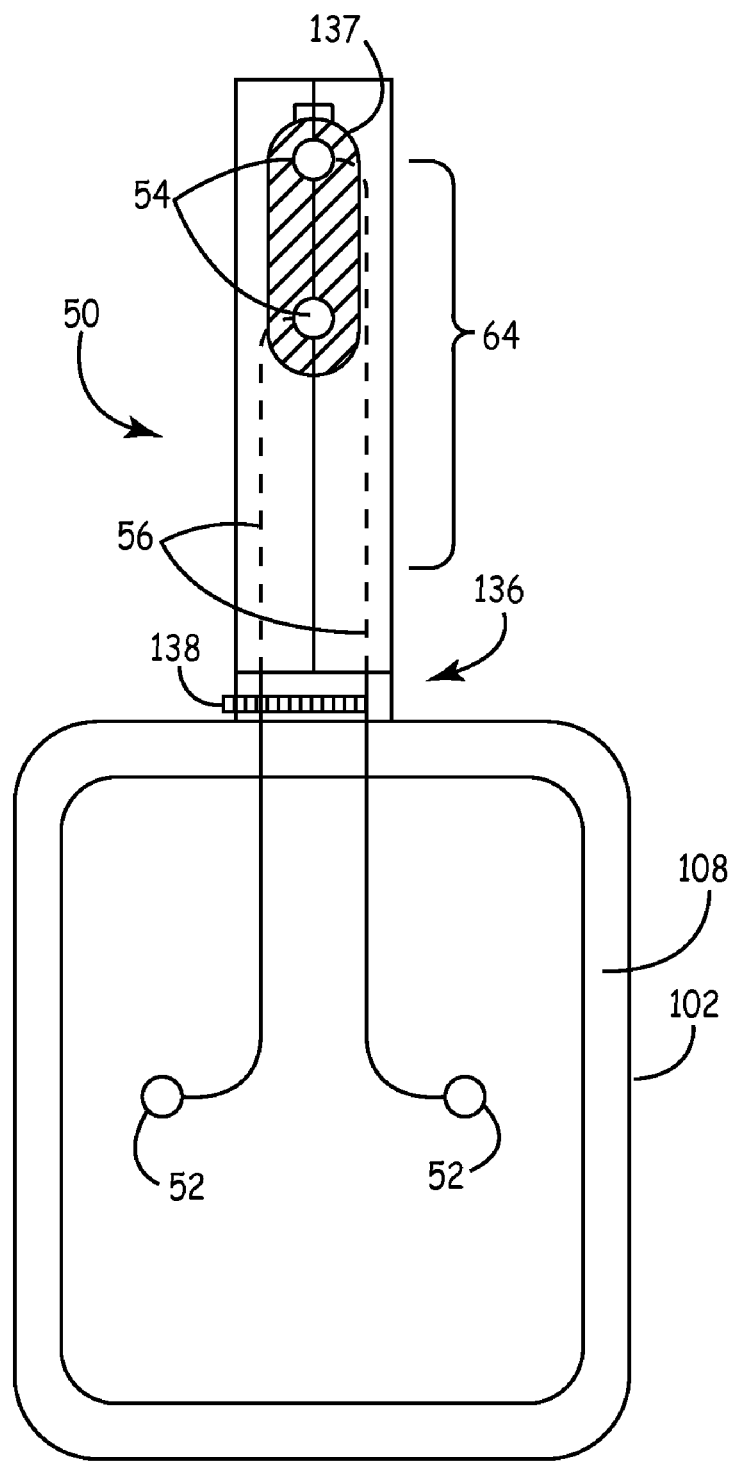
FIG. 10C is a top view of the electrical interface shown in FIG. 10B further including elements for protecting the electrical interface.

FIG. 10C is a top view of the electrical interface shown in FIG. 10B further including elements for protecting the electrical interface. In some embodiments, a removable patient terminal insulator 137 may be provided for protecting patient terminals 54 from mechanical damage or wear and/or to prevent unwanted electrical signals to be coupled through to the IMD electronics via terminals 54. Removable patient terminal insulator 137 may be provided, for example, in the form of a removable tape that is pulled away to expose patient terminals at the time of pre-implant testing or other use of electrical interface 50. Patient terminal insulator 137 may be provided as a replaceable element such that after testing is completed, insulator 137 may be placed back over patient terminals 54.

A removable short circuit element 138 may be provided across conductors 56 so as to prevent unwanted electrical signals from reaching the IMD electronics. Short circuit element 138 may be provided, for example, as a strip of conductive tape extending across conductors 56 which can be removed at the appropriate time to enable pre-implant testing or other use of electrical interface 50. Short circuit element 138 may be provided as a replaceable element such that after testing is completed, short circuit element 138 can be put back in place to create a short across conductors 56.

Figure 11:
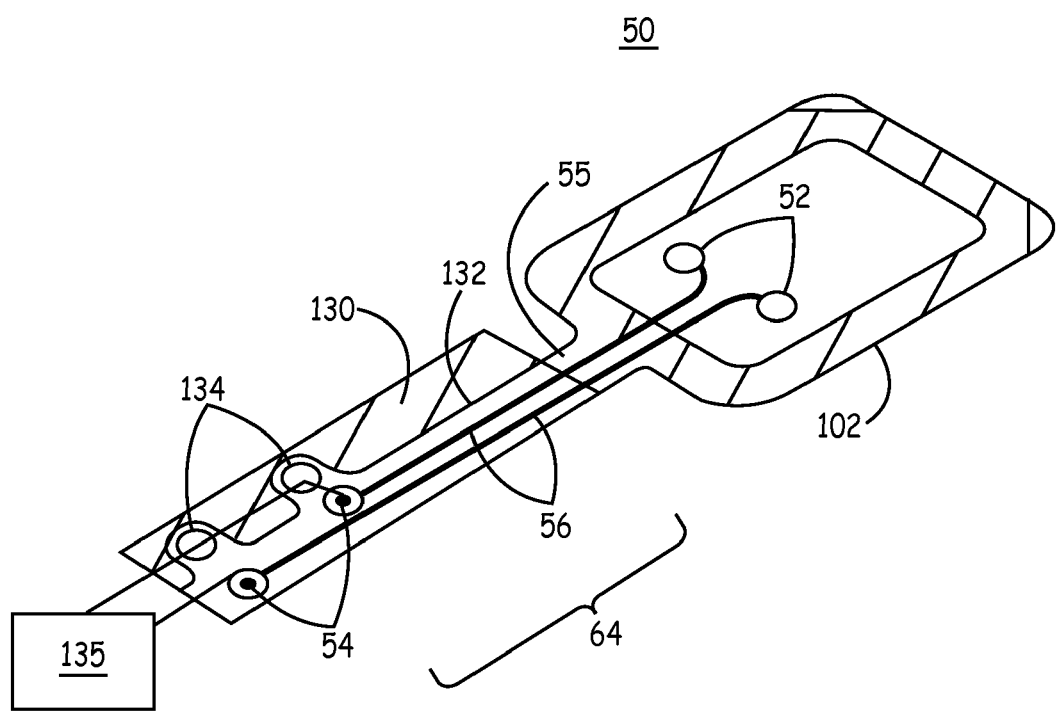
FIG. 11 is a perspective view of an alternative embodiment of an electrical interface.

FIG. 11 is a perspective view of an alternative embodiment of an electrical interface. Substrate 55 is provided with a single lateral flap 130 along neck 64 sized to cover and insulate conductors 56 after folding lateral flap 130 along folding line 132. Windows 134 are provided in lateral flap 130 such that patient terminals 54 remain exposed after folding lateral flap 130 over conductors 56. Lateral flap(s) 130 as shown in FIG. 10B and 11 may be laminated to neck 64 or sealed to neck 64 using the same method for sealing inner tray lid 102 to an inner tray. In FIG. 11, patient terminals 54 are shown to include connection members 135, which may be in the form of snaps or clips, to facilitate connection of electrode leads or cable extensions as described previously.

While FIGS. 8 through 11 depict electrical interface 50 formed on an inner surface of inner tray lid 102, it is recognized that electrical interface 50 may be formed on any inner surface of package 60 so long as package contacts 52 become electrically coupled to IMD electrodes 14. For example, in some embodiments, the IMD may be configured and contained within an inner tray such that contact with an electrode terminal 15 (shown in FIG. 4A) is best made from an inner surface of the inner tray rather than the tray lid. In such a configuration, package contact 52 and a portion of the conductor circuit 53 may be formed on an inner surface of the inner tray instead of the tray lid.

Figure 12:
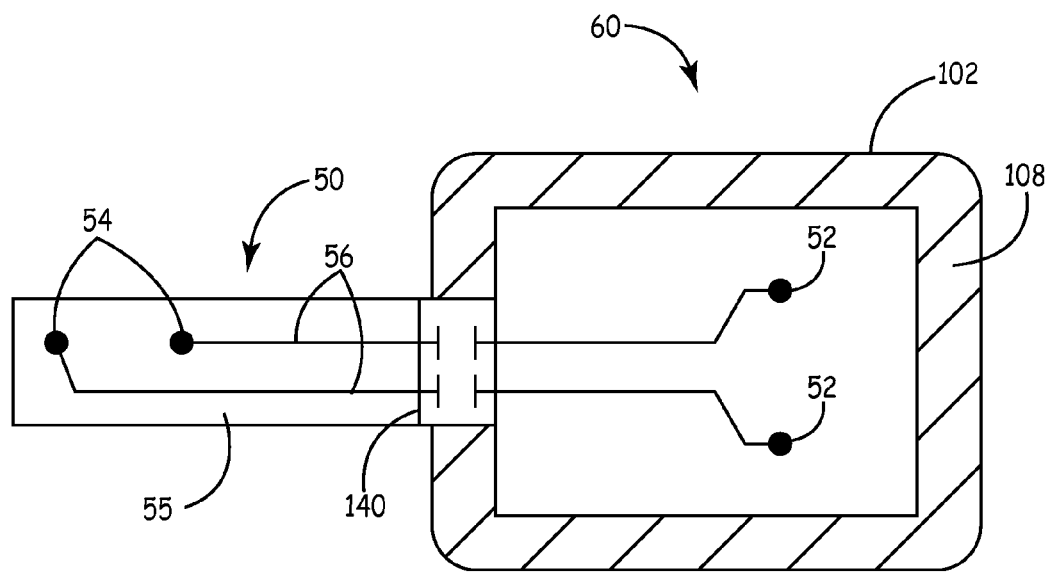
FIG. 12 is a diagram of an alternative embodiment of an electrical interface used for connecting to IMD electronics while the IMD is within sterile packaging.

FIG. 12 is a diagram of an alternative embodiment of an electrical interface used for connecting to IMD electronics while the IMD is within sterile packaging. Conductor circuit 53 includes conductors 56 and capacitive elements 140 used to conduct signals across seal area 108 of package 60. It is recognized that conductive circuit 53 may include any circuitry used to convey signals sensed using patient terminals 54 to package contacts 52. A capacitive element 140 may be used to conduct signals across a sterile barrier of package 60. The inner tray wall or the seal area 108 may serve as a dielectric in the capacitive element 140. A conductor circuit 53 including a capacitive element 140 may protect the patient and/or IMD from noise or signal baseline variation that may be induced on conductors 56.

Figure 13:
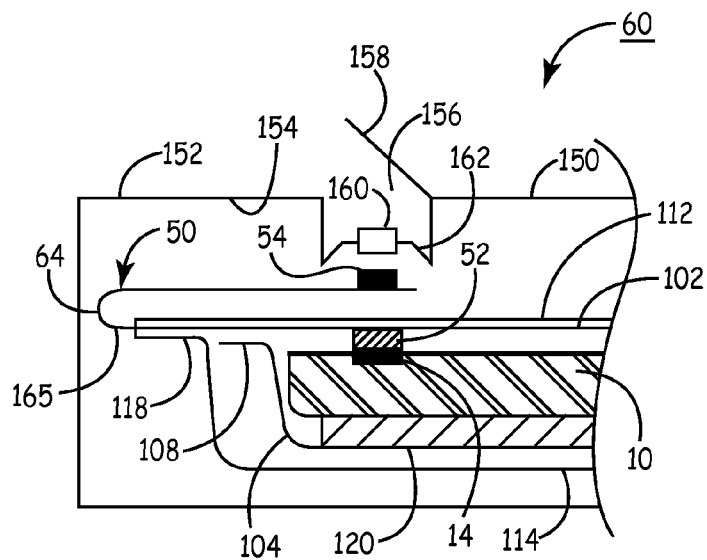
FIG. 13 is a partial, side cut-away view of a packaging system according to another embodiment of the invention.

FIG. 13 is a partial, side cut-away view of a packaging system according to another embodiment of the invention. Package 60 includes sterilizable inner tray 104 containing IMD 10 having subcutaneous electrode 14. Inner tray 104 is sealed closed along seal area 108 with tray lid 102. Tray lid 102 serves as the substrate for electrical interface 50 including package contact 52 positioned to provide electrical contact with electrode 14. Electrical interface 50 further includes elongated conductors 56 as shown previously extending to patient terminal 54. Electrical interface 50 is shown in a folded arrangement over an outer tray lid 112 sealed to outer tray 114, containing inner tray 104. An outer carton 150 is provided for containing outer tray 114 and electrical interface 50.

A strain relief member 165 is shown in FIG. 13 extending from neck 64 to an outer surface of outer tray 114. Strain relief member 165 may be coupled to any portion of package 60 to provide strain relief to the portion of neck 64 crossing seal areas 118 and 108. Strain relief member 165 may prevent inadvertent breach of the outer tray seal or inner tray seal when patient terminals 54 are being attached or repositioned on a patient.

Outer carton 150 has an inner surface 154 and an outer surface 152 which form a recess 156 in which a carton contact 160 is mounted on a compressible member 162. When carton contact 160 is pressed down, carton contact 160 makes electrical contact with patient terminal 54. Carton contact 160 may be provided with a snap or clip member to facilitate attaching an external electrode extension or cable. Connection to the electronics within IMD 10 is thereby made possible via carton electrode 160 and electrical interface 50 while IMD 10 remains inside sterilized inner tray 104, outer tray 114 and outer carton 150. It is recognized that in various embodiments, other signal conveying elements may be added to or substituted for carton electrode 160, such as capacitive elements, inductive elements, optical fibers, or antennas.

Carton 150 may be formed with a closing member 158, such as a closable flap or resealable tape that can be closed over recess 156 to protect carton electrode 160. It is recognized that numerous configurations may be conceived for incorporating a carton electrode 160 in outer carton 150. For example, in other embodiments, carton electrode 160 may be located along outer surface 152 extending through to inner surface 154 without being positioned in a recess 156. It is further recognized that a removable insulating layer may be provided over carton electrode 160. In some embodiments, compression member 162 may not be provided, and the normal position of carton contact 160 may be in electrical contact with patient terminal 54. An insulating material over carton contact 160 may or may not be used.

Figure 14:
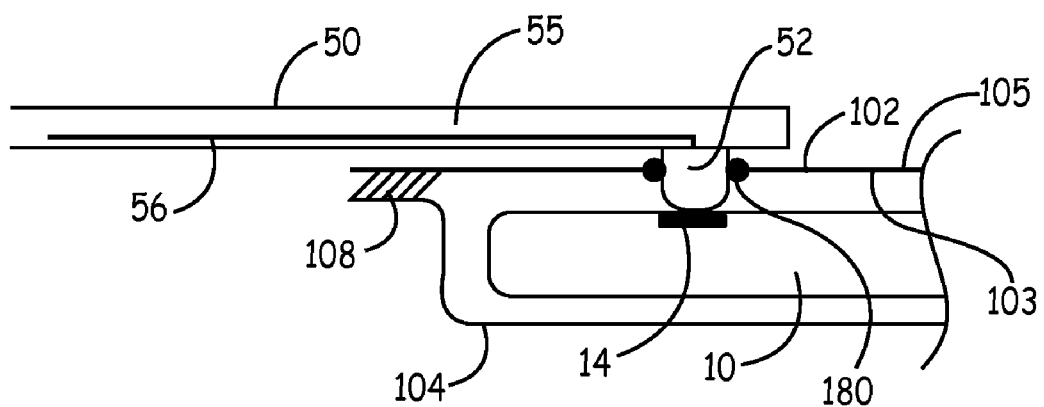
FIG. 14 is a partial, side cut-away view of an electrical interface provided with a substrate that extends along the outer surface of a package tray lid.

FIG. 14 is a partial, side cut-away view of an electrical interface 50 provided with a substrate 55 that extends along the outer surface 105 of tray lid 102. Electrical interface 50 includes a package contact 52 formed extending through tray lid 102 to make electrical contact with IMD subcutaneous electrode 14. In an alternative embodiment, a separate substrate 55 is not used and electrical interface 50 is formed on the outer surface 105 of tray lid 102. Conductor 56 would extend along tray lid outer surface 105 to package contact 52 which would extend through tray lid 102 to make electrical contact with IMD electrode 14. Alternatively, elongated conductor 56 may extend through tray lid 102. Conductor 56 may be provided as a conductive wire, foil, or film that penetrates tray lid 102 or may include an capacitive or inductive element for conveying current across tray lid 102. It is recognized that in various embodiments, any element of electrical interface 50 may extend across a sterile barrier, i.e., from an outer surface to an inner surface of a sterilizable IMD package, along any portion of the package and is not limited to extending across a seal area of the package.

Furthermore, the electrical interface 50 may be formed on a substrate extending along any outer or inner surface of the sterilizable IMD package, including an outer or inner surface of any tray, tray lid, pouch or other sterilizable IMD package. Alternatively, electrical interface 50 may be fabricated using a separate substrate 55, which likewise may extend along any outer or inner surface of the sterilizable IMD package. The exact configuration of electrical interface 50 with respect to the IMD package 60 may vary from embodiment to embodiment depending on the orientation of the IMD within the package and the resulting location of IMD electrodes or electrode terminals with which package contact(s) 52 are to be electrically coupled.

Figure 15:
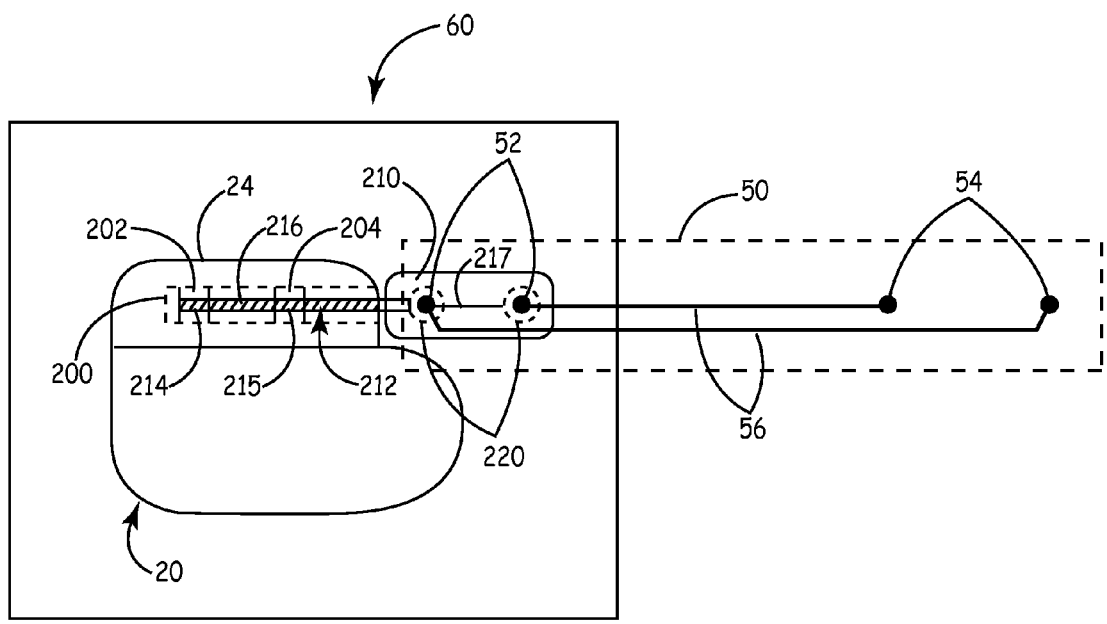
FIG. 15 is a plan view of an IMD in a sterilizable package provided with an interface for accessing IMD electronics according to another embodiment of the invention.

FIG. 15 is a plan view of an IMD in a sterilizable package provided with an electrical interface for accessing IMD electronics according to another embodiment of the invention. Some IMDs may be used in conjunction with electrodes carried by leads extending from the IMD rather than being incorporated on the IMD housing. IMD 20 is shown having connector header 24 provided with a connector bore 200 adapted for receiving a connector assembly of a lead carrying one or more electrodes or other sensors. Connector header and lead connector assembly configurations are known in the art. In the example shown, connector bore 200 is provided with contacts 202 and 204 for coupling with connectors included on a lead connector assembly.

To facilitate electrical connection to electrical interface 50, IMD 20 may be packaged within sterilizable package 60 with a connector appliance 210 inserted into connector bore 200. Connector appliance 210 is provided with a connector assembly 212 adapted for insertion into connector bore 200. Connector assembly 212 includes two connectors 214 and 215 separated by an insulating segment 216. Connectors 214 and 215 align with and become electrically coupled to contacts 202 and 204 when connector assembly 212 is fully inserted in connector bore 200. Connector assembly 212 of connector appliance 210 generally corresponds to a connector assembly provided on a lead intended for use with IMD 20. Connector appliance 210 is provided with electrode contacts 220 which are separately coupled to each of connectors 214 and 215 by conductors 217 extending through appliance 210. Package contacts 52 included on electrical interface 50 are positioned over electrode contacts 220 such that patient terminals 54, located outside of package 60, can be coupled to the electronics included in IMD 20 via connector appliance 210. Alternatively, conductors 217 may extend along a substrate to the outside of package 60 directly to patient terminals 54, without the use of package contacts 52.

Patient terminals 54 may be positioned on or in a patient or coupled to electrodes or any other physiological sensors positioned on or in a patient via appropriate leads or extension cables. As such, electrical interface 50 may be used to access IMD electronics included in an IMD having a connector header 24 with the use of a connector appliance 210.

Figure 16:
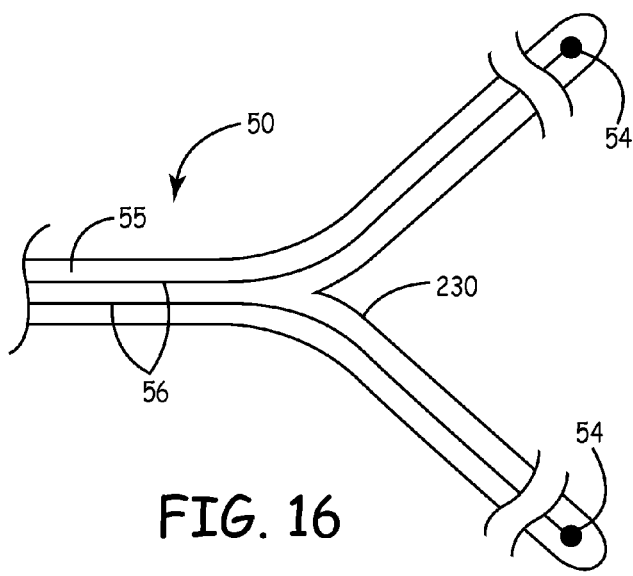
FIG. 16 illustrates a bifurcated electrical interface.

FIG. 16 illustrates a bifurcated electrical interface. In some embodiments, two or more electrodes carried by branching or separate leads may be placed independently of each other. An electrical interface 50 may be provided with a bifurcation 230 such that patient terminals 54 may be placed at separate, spaced apart locations. It is recognized that substrate 55 may be provided with numerous shapes or configurations for allowing placement of patient terminals 54 during pre-implant testing in any appropriate manner that mimics placement of the actual electrodes to be used in conjunction with the IMD. Alternatively, patient terminals 54 may be connected to separate electrode extensions that allow unencumbered placement of electrodes on the patient during pre-implant testing, as described previously.

For the sake of illustration, various embodiments described herein have generally related to an electrical interface that allows connection to IMD electronics for pre-implant testing relating to optimizing subcutaneous electrode placement. However, it is recognized that an electrical interface used to access the electronics within an IMD still contained in a sterile package may be designed to mimic electrodes/sensors adapted for other implant locations, e.g., epicardial, endocardial, sub-muscular, or otherwise. As such, embodiments that include using an electrical interface for testing non-subcutaneous implant locations of an IMD or electrodes/sensors are included in the scope of the invention. Pre-implant testing using the interface may be performed to determine if the patient meets implant criteria and/or selecting an optimal implant site.

Various embodiments of the electrical interface 50 shown in FIG. 4A have been described primarily in the context of an interface used to couple electrodes, for example ECG electrodes, to an IMD electronics module across a sterile barrier. However, the electrical interface 50 may be used to couple any type and number of electrodes and/or sensors to the IMD electronics. Furthermore, electrical interface 50 may be used for purposes other than pre-implant testing. Electrical interface 50 may be used, for example, for performing IMD system tests or for demonstration purposes.

Packaging systems having an interface that allows access to IMD electronics across a sterile barrier have been presented in the foregoing description with reference to specific embodiments. It is appreciated that various modifications to the referenced embodiments may be made without departing from the scope of the invention as set forth in the following claims.

The invention claimed is:

1. A system, comprising:
 a sterilized package; and
 an implantable medical device (IMD) placed inside the sterilized package, the IMD having a housing with two or more subcutaneous electrodes positioned on an exterior surface of the housing and spaced from one another by a first distance;
wherein
 the sterilized package comprises:
 a. two electrodes adapted for placement directly on a patient and spaced from one another by the first difference; and
 b. an electrical interface, including a flexible substrate, for conveying a physiological signals from the electrodes to the subcutaneous electrodes on the implantable medical device housing within the sterilized package without compromising the sterility of the implantable medical device.

2. The system of claim 1 wherein disposed on the flexible substrate are any of the following: conductive ink, conductive foil, conductive film, and conductive tape.

3. The system of claim 1 further including means for transmitting signals received by the implantable medical device from the conveying means electrical interface to an external device.

4. The system of claim 1 further including:
 a computerized database;
 a communication network coupled to the database;
 means for transmitting data from the implantable medical device to the database via the communication network.

5. The system of claim 1 wherein further including means for processing signals received by the implantable medical device using the conveying means electrical interface.

6. The system of claim 5 wherein the implantable medical device further includes means for generating a signal corresponding to the signals received by the implantable medical device using the conveying means electrical interface.

7. The system of claim 1 wherein the sterilizable package includes an inner surface and an outer surface and wherein the conveying means electrical interface is formed on a portion of any of: the inner surface and the outer surface.

8. The system of claim 1 wherein the sterilized package includes a device tray and a tray lid sealed to the device tray.

9. The system of claim 1 further including means for generating pressure for promoting electrical contact between the conveying means electrical interface and the electrodes on the housing of the implantable medical device.

10. The system of claim 1 wherein the conveying means electrical interface includes a template corresponding to the shape of the implantable medical device.

11. The system of claim 10 wherein the template includes means for facilitating marking of a selected implant arrangement.

12. The system of claim 1 wherein the conveying means electrical interface includes a means for insulating any portion of the conveying means electrical interface.

13. The system of claim 1 wherein the conveying means electrical interface includes means for creating a short circuit across the conveying means electrical interface for protecting the implantable medical device from electrical signals when the conveying means electrical interface is not in use.

14. The system of claim 1 wherein the conveying means electrical interface includes means for relieving mechanical strain across the conveying means electrical interface.

15. The system of claim 1 further including an outer carton containing the sterilized package and means for electrically coupling to the conveying means electrical interface from outside of the outer carton.

16. The system of claim 1 wherein the conveying means electrical interface includes means for indicating electrical signal conduction by the conveying means electrical interface.

* * * * *

UNITED STATES PATENT AND TRADEMARK OFFICE
CERTIFICATE OF CORRECTION

PATENT NO.         : 8,219,200 B2
APPLICATION NO.    : 12/825798
DATED              : July 10, 2012
INVENTOR(S)        : William K. Wenger et al.

It is certified that error appears in the above-identified patent and that said Letters Patent is hereby corrected as shown below:

Col. 16, line 61, delete "...the conveying means electrical interface..." and insert in place thereof
-- the electrical interface --
Col. 17, line 5, delete "...the conveying means electrical interface..." and insert in place thereof
-- the electrical interface --
Col. 17, Line 7, delete "...the conveying means electrical interface..." and insert in place thereof
-- the electrical interface --
Col. 17, Line 9, delete "...the conveying means electrical interface..." and insert in place thereof
-- the electrical interface --
Col. 17, Line 15, delete "...the conveying means electrical interface..." and insert in place thereof
-- the electrical interface --
Col. 17, Line 18, delete "...the conveying means electrical interface..." and insert in place thereof
-- the electrical interface --
Col. 18, Line 2, delete "...the conveying means electrical interface..." and insert in place thereof
-- the electrical interface --
Col. 18, Line 5, delete "...the conveying means electrical interface..." and insert in place thereof
-- the electrical interface --
Col. 18, Line 8, delete "...the conveying means electrical interface..." and insert in place thereof
-- the electrical interface --
Col. 18, Line 10, delete "...the conveying means electrical interface..." and insert in place thereof
-- the electrical interface --
Col. 18, Line 11, delete "...the conveying means electrical interface..." and insert in place thereof
-- the electrical interface --
Col. 18, Line 14, delete "...the conveying means electrical interface..." and insert in place thereof
-- the electrical interface --

Signed and Sealed this
Fourth Day of December, 2012

David J. Kappos
*Director of the United States Patent and Trademark Office*